(12) United States Patent
Gorodetsky

(10) Patent No.: US 8,354,111 B2
(45) Date of Patent: Jan. 15, 2013

(54) STABLE CELL BINDING CHIMERIC PEPTIDES

(75) Inventor: Raphael Gorodetsky, Jerusalem (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 12/937,344

(22) PCT Filed: Apr. 16, 2009

(86) PCT No.: PCT/IL2009/000420
§ 371 (c)(1),
(2), (4) Date: Dec. 27, 2010

(87) PCT Pub. No.: WO2009/128077
PCT Pub. Date: Oct. 22, 2009

(65) Prior Publication Data
US 2011/0111003 A1     May 12, 2011

Related U.S. Application Data

(60) Provisional application No. 61/044,513, filed on Apr. 14, 2008.

(51) Int. Cl.
*A61K 39/00* (2006.01)
*A61K 38/04* (2006.01)
(52) U.S. Cl. ...... 424/185.1; 530/324; 514/1.1; 514/21.3
(58) Field of Classification Search .................. None
See application file for complete search history.

(56) References Cited

U.S. PATENT DOCUMENTS

| 7,122,620 B1 | 10/2006 | Gorodetsky et al. |
| 7,148,190 B2 | 12/2006 | Marx et al. |

FOREIGN PATENT DOCUMENTS

| WO | 92/01464 A1 | 2/1992 |
| WO | 01/53324 A1 | 7/2001 |
| WO | 03/044172 A1 | 5/2003 |
| WO | 2004/041298 A1 | 5/2004 |
| WO | 2009/022340 A1 | 2/2009 |

OTHER PUBLICATIONS

Durell et al. What studies of fusion peptides tell us about viral envelope glycoprotein-mediated membrane fusion. Mol Membr Biol. Jul.-Sep. 1997;14(3):97-112.*
Sergel et al. Mutations in the Fusion Peptide and Adjacent Heptad Repeat Inhibit Folding or Activity of the Newcastle Disease Virus Fusion Protein. J. Virol. 2001 vol. 75 No. 17 7934-7943.*
Nasu et al. Expression of wild-type and mutated rabbit osteopontin in *Escherichia coli*, and their effects on adhesion and migration of P388D1 cells. Biochem. J. (1995) 307, 257-265.*
Wikipedia, FGL1. Mar. 20, 2012, pp. 1-3.*
Skolnick et al. From genes to protein structure and function: novel applications of computational approaches in the genomic era. Trends Biotechnol. 18(1):34-9, 2000.*
Attwood TK. Genomics. The Babel of bioinformatics. Science. 290(5491):471-473, 2000.*
Brenner SE. Errors in genome annotation. Trends in Genetics 15:132-133, 1999.*
Bork Powers and pitfalls in sequence analysis: the 70% hurdle. Genome Res. Apr. 2000;10(4):398-400.*
Gorodetsky, Raphael et al., "Fibrin Microbeads (FMB) as Biodegradable Carriers for Culturing Cells and for Accelerating Wound Healing", Journal of Investigative Dermatology, 112(6):866-872 (1999).
Gorodetsky, Raphael et al., "New cell attachment peptide sequences from conserved epitopes in the carboxy termini of fibrinogen", Experimental Cell Research, 287(1):116-129 (2003).
Levy, Liron et al., "Fibrinogen-derived peptides that mediate cell adhesion: structure and activity studies", Journal of Peptide Science 14(8 Suppl1):173-174, 30th European Peptide Symposium; Helsinki, Finland Aug. 31-Sep. 5, 2008.
Marx, Gerard et al., "Fibrinogen C-terminal peptidic sequences (Haptides) modulate fibrin polymerization", Thrombosis and Haemostasis, 91(1):43-51 (2004).
Ohnishi, Shunsuke et al., "Radiolabeled and near-infrared fluorescent fibrinogen derivatives create a system for the identification and repair of obscure gastrointestinal bleeding", Surgery, 14(5):785-792 (2006).
Ugarova, Tatiana P. et al., "Recognition of Fibrinogen by Leukocyte Integrins", Annals of the New York Academy of Science, 936:368-385 (2001).
International Search Report for PCT/IL2009/000420 dated Aug. 12, 2009.

* cited by examiner

*Primary Examiner* — Maher Haddad
(74) *Attorney, Agent, or Firm* — Rodney J. Fuller; Booth Udall Fuller, PLC

(57) ABSTRACT

The present invention relates to novel family of homologous cell attachment chimeric peptides. In particular, the present invention relates to chimeric peptides, each comprising synthetic peptides comprising (a) an M-tide comprising an amino acid sequence that is at least 80% homologous to the amino acid sequence selected from the group consisting of: SEQ ID NO:1, 2 and 37; and (b) a core haptide comprising an amino acid sequence homologous to amino acid sequences at the carboxy termini of the and E chains of fibrinogen or other proteins comprising C-termini that are homologous to said fibrinogen sequences, wherein the M-tide and the core haptide originate from the same protein. The synthetic peptides are linked to one another thereby providing the chimeric peptides of the invention which does not occur in the native protein as a continuous sequence. The present invention further discloses pharmaceutical compositions comprising said chimeric peptides and uses thereof.

12 Claims, 16 Drawing Sheets

| Species | Address | AA sequence | SeqID |
|---|---|---|---|
| Human | 206-232 | V Y C E I D G S G N G W T V F Q K R L D G S V D F K K | 10 |
| Bovine | 203-229 | V V C E I D G S G N G W T V F Q K R L D G S V D F K K | 45 |
| Chicken | 206-232 | V Y C E I D T Y G N G W T V L Q R R L D G S E D F F R | 46 |
| Rat | 206-232 | V Y C E T D G P G N G W T E F K K R L D G S V D F L K | 47 |
| Sea Lamprey | 205-230 | V Y C E I E N G - G W T V I Q H R H D G S V N F T F | 48 |

Fig. 1A

| Protein | AA sequence | Homology | Address | SID |
|---|---|---|---|---|
| Fibrinogen γ | V Y C E I D G S G N G W T V F Q K R L D G S V D F K K | 19/27 | 206-232 | 10 |
| Fibrinogen β | V Y C D M T S D G G G W T V I Q N R Q D G S V D F G R | 27/27 | 268-294 | 11 |
| Tenascin C | V Y C H M T E N G G G W T V I Q R R E N G Q T D F F R | 18/27 | 2012-2036 | 12 |
| Tenascin X | V Y C H T T D G G G W T V I V R R K D G R E N F F R | 18/27 | 487-513 | 13 |
| Tenascin R | V Y C D M T T D G G G W T V I Y Q R R Q N G Q T D F F R | 19/27 | 1166-1192 | 14 |
| ANG 1 | V Y C D M N T E N G G W T V I Q H R E D G S L D F Q R | 22/27 | 313-339 | 15 |
| ANG 2 | V Y C D M N T A G G G W T V I Q R R E D G S V D F Q R | 19/27 | 312-337 | 16 |
| MFA | V Y C D M T T E G G K W T V F Q K R F N G S V E F F R | 19/27 | 68-94 | 17 |

Fig. 1B

| Tested ligand/SID | NH$_2$— | | | | | | | | | | —COOH | | | Homolog + similar | Address |
|---|---|---|---|---|---|---|---|---|---|---|---|---|---|---|---|
| Fibrin Related Haptides – Inter-peptide Homology | | | | | | | | | | | | | | | |
| PreCγ /26 | K | T | R | W | Y | S | M | K | I | P | N | R | L | 17/20 | 373-392 / 411 |
| Cβ /30 | K | G | S | W | Y | S | M | K | K | P | F | P | Q | 17/21 | 441-461 / 461 |
| CαE /24 | R | G | A | D | Y | S | | | | | | | | | |
| | | | | | | | | | | | | | | | |
| | | | | | | | | | | | | | | | |
| | | | | | | | | | | | | | | | |
| | | | | | | | | | | | | | | | |
| Legend |
| ■ Full homology  ▨ Low similarity |
| ▨ High similarity  ▨ No similarity |
| ⇒ More residues at the C-terminal |
| ] C-terminal end |

Fig. 2A

| Tested ligand/SID | 10mer Haptides – Inter-peptide Homology ⇐NH2  COOH⇒ | | | | | | | | | | Homolog + similar | Address |
|---|---|---|---|---|---|---|---|---|---|---|---|---|
| PreCγ /18 | K | T | R | W | Y | S | M | K | T | T | 7/10 | 373-382 / 411 |
| Cβ /23 | K | G | S | W | Y | S | M | F | K | S | 7/10 | 441-450 / - |
| Non-Fibrinogen 10mer Haptides Homology to preCγ and/or Cβ and/or CαE | | | | | | | | | | | | |
| CtenX /21 | K | G | F | E | F | S | V | P | F | E | 5/10 | 1672-1690/ 1697 |
| Cang1 /19 | K | G | P | S | Y | S | L | R | S | T | 6/10 | 479-488 /497 |
| Cmfa /22 | K | G | F | S | Y | S | L | K | T | E | 7/10 | 239-248 /255 |

Legend
- ■ Full homology
- ▨ High similarity
- ⊠ Low similarity
- ☐ No similarity

Fig. 2B

Fig. 3B
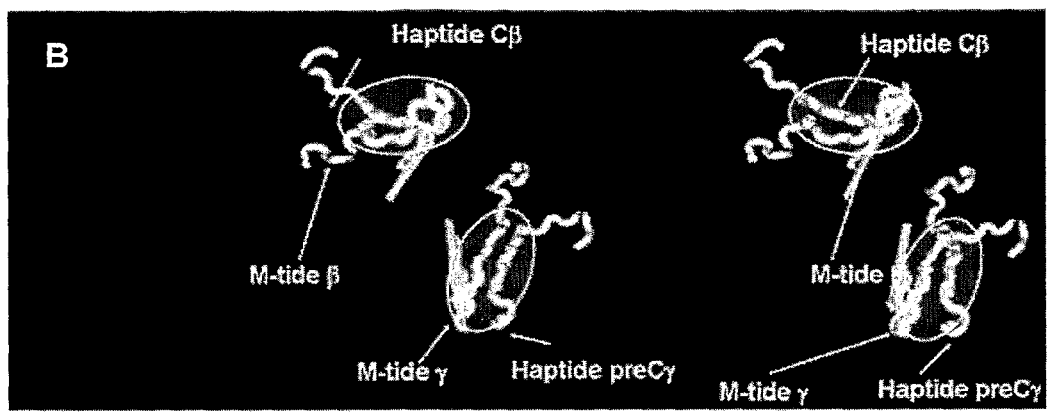
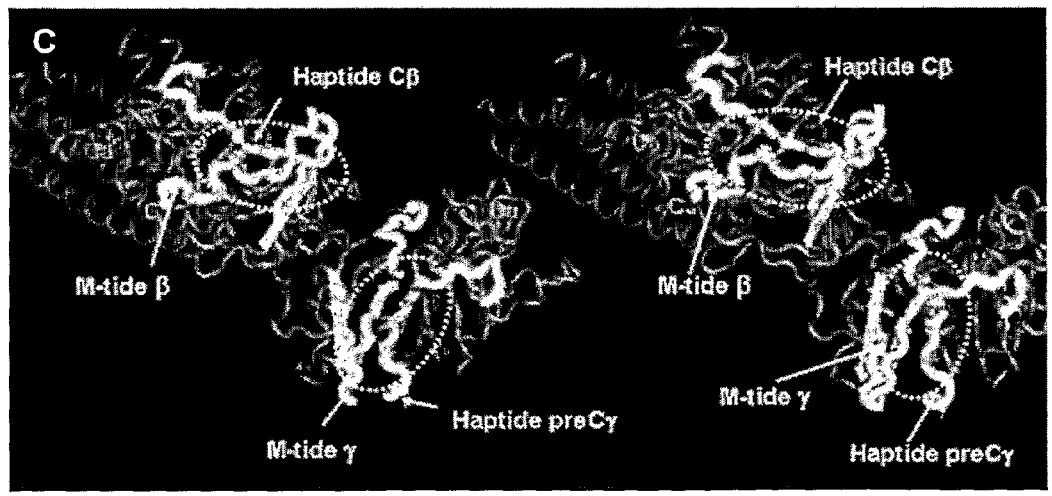
Fig. 3C

STABLE CELL BINDING CHIMERIC PEPTIDES

RELATED APPLICATION DATA

This application is the U.S. national stage of PCT/IL2009/000420, filed Apr. 16, 2009, which claims the benefit of U.S. Provisional Application No. 61/044,513, filed Apr. 14, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,507 byte ASCII (text) file named "Seq_List" created on Oct. 11, 2010.

FIELD OF THE INVENTION

The present invention relates to novel cell attachment chimeric peptides. In particular, the present invention relates to chimeric peptides, each comprising synthetic peptides comprising amino acid sequences homologous to portions of the carboxy termini of fibrinogen chain or other proteins, with the proviso that the amino acid sequences in each chimeric peptide are homologous to portions of the same protein. The synthetic peptides are based on linking the sequences, that are naturally co-located in the 3D structure of fibrinogen chains $\beta$ and $\gamma$, as a beta-sheet, thereby providing the chimeric peptides of the invention. The present invention further discloses pharmaceutical compositions comprising said chimeric peptides and uses thereof.

BACKGROUND OF THE INVENTION

Fibrinogen is the plasma protein responsible for blood clot formation. Normal fibrinogen is a complex of two chains, out of the $\alpha$, $\beta$ and $\gamma$ chains. About 1% of the total fibrinogen in adult humans contains a variant of a fibrinogen (also termed $fib_{340}$), known as $\alpha E$ fibrinogen ($fib_{420}$), which has an extended a chain. The four types of fibrinogen chains, $\alpha$, $\beta$, $\gamma$ and $\alpha E$, contain 610, 483, 411 and 866 amino acids, respectively (the numbering based on the Gene-bank database, accessible at ncbi.nlm.nih.gov).

Fibrinogen is not immunogenic within the same species, as attested by the use of pooled fibrin glue for clinical applications. Besides its hemostatic activity, it has been previously demonstrated that fibrin(ogen) elicits cell attachment (haptotactic) and migratory (chemotactic) responses with different cell types including mouse and human fibroblasts (MF and HF), bovine aortic endothelial cells (BAEC) and smooth muscle cells (SMC).

The carboxy terminal sequences, i.e., the C-terminal 30-40 amino acids of the fibrinogen chains, are highly conserved between different species. This region, which is termed FRED (fibrinogen related domain), is present also at the end of the C-terminus domains of some non-fibrin related proteins, such as, tenascins, angiopoietins, and microfibril associated protein 4 (MFA4).

U.S. Pat. Nos. 7,122,620 and 7,148,190 of the inventors of the present invention, incorporated herein by reference, disclose isolated peptides (hereinafter "haptides") with homologous sequences corresponding to sequences of 19-21 amino acids in the carboxy termini regions of the $\beta$, $\gamma$ and $\alpha E$ chains of fibrinogen (peptides termed $c\beta$, $C\gamma$ and $C\alpha E$ respectively), or from other protein comprising regions in the C-termini that are homologous to the fibrinogen sequences of $C\beta$, $preC\gamma$ or $C\alpha E$. These include microfibril-associated protein-4, members of the angiopoietin I and II protein families and tenascins, a family of extracellular proteins. Haptides were shown to induce haptotactic responses in various cultured cell types, mostly of mesenchymal origin, such as HF, BAEC and SMC. Some of the haptides, for example—$C\beta$, were shown to be rapidly taken up by the cells in a non-saturatable manner. None of the haptides affected the rate of cell proliferation.

There is a recognized need for, and it would be highly advantageous, to design synthetic haptotactic peptides having improved stability which contain an active part of the haptide sequence linked to part of the M-tide that stabilizes it. This does not require the presence of the entire fibrin(ogen) or other proteins containing the haptotactic peptides to attach cells.

SUMMARY OF THE INVENTION

The present invention relates to novel cell attachment chimeric peptides comprising two short amino-acid sequences, namely, (i) a first haptotactic sequence (hereinafter "corehaptide") comprising an amino acid sequence homologous to 13mer out of the homologous 19-21 amino acid sequence in the carboxy termini of the fibrinogen chains, particularly the carboxy termini of the $\beta$, $\gamma$ and $\alpha E$ chains of fibrinogen, or other proteins comprising C-termini that are homologous to said fibrinogen sequences; and (ii) a second peptide (hereinafter "M-tide") derived from a larger sequence (hereinafter "full length M-tide") homologous sequences between the aforementioned chains of fibrinogen, or other proteins comprising C-termini that are homologous to said fibrinogen sequences, that are also highly conserved between species, wherein the second sequence by itself is not necessarily highly cell binding (haptotactic). Moreover, said first and second sequences that together form the chimeric peptides of the invention are homologous to short sequences in the same fibrinogen chain, however, there is no sequence homology between said first and second sequences themselves. Nevertheless, in a 3-dimensional structure the fibrinogen chains, the natural sequences corresponding to said first and second sequences are folded so that they are located in the folded protein in close proximity to form a beta-sheet structure. The synthetic chimeric peptides of the invention are capable of enhancing haptotaxis. Moreover, the peptides of the invention exhibit exceptionally high stability, higher than the stability of Haptides. The present invention further relates to pharmaceutical compositions comprising peptidic sequences based on the proposed chimeric peptides of the invention and methods of using same for treating a subject in need thereof.

The present invention is based in part on the unexpected finding that although the portions of the M-tides which is integrated in the new invented peptides do not have major haptotactic activity, in comparison to the haptotactic activity of the corresponding haptides, linking part of the M-tides to the active portion of the haptides results in chimeric peptides that are highly haptotactic. Another surprising feature of the chimeric peptide of the invention is their higher stability relative to the stability of the corresponding haptide sequences. The chimeric peptides of the invention were found to maintain activity weeks after being stored at room temperature.

According to one aspect, the present invention provides a chimeric peptide comprising an M-tide sequence comprising an amino acid sequence that is at least 70% homologous to the amino acid sequence selected from the group consisting of: VFQKR LDGSV DFKK (m-γ 14-mer, SEQ ID NO:1); VIQNR QDGSV DFGR (m-β14-mer, SEQ ID NO:2) and LIQQR MDGSL NFNR (m-αE 14-mer, SEQ ID NO:37) and a portion of at least 13 residues from the n-termini of the 19-21 amino acids containing haptides equivalent to the carboxy termini of the β, γ and αE chains of fibrinogen or of other proteins comprising C-termini that are homologous to said fibrinogen sequences, wherein the M-tide and the haptide originate from the same protein chain.

Without wishing to be bound by any particular concept or mechanism of action, the finding that each of the chimeric peptides of the invention maintains haptotactic activity and moreover exhibits an improved activity and stability may be associated with the 3-D conformation of the two sequences, forming the chimeric peptide, in their native conformation within the entire protein from which they are derived. For example, the M-tides and core haptides in the beta and gamma chains of fibrinogen and in other molecules such as angiopoietin and tenascin, are always folded in parallel to one another to form a beta-sheet structure (FIG. 3).

According to one embodiment, the protein from which the M-tide and core haptide originate is selected from the group consisting of: fibrinogen, tenascin, angiopoietin and microfibril-associated glycoprotein (MFA).

According to one embodiment, the M-tide comprises a sequence that is at least 80% homologous to, preferably 85% homologous to, more preferably 90% homologous to, an amino acid sequence selected from the group consisting of: VFQKR LDGSV DFKK (m-γ 14-mer, SEQ ID NO:1); VIQNR QDGSV DFGR (m-β 14-mer, SEQ ID NO:2) and LIQQR MDGSL NFNR (m-αE 14-mer, SEQ ID NO:37).

According to yet another embodiment, the M-tide comprises an amino acid sequence selected from the group consisting of: VFQKR LDGSV DFKK (m-γ 14-mer, SEQ ID NO:1); VIQNR QDGSV DFGR (m-β 14-mer, SEQ ID NO:2); VFLRR KNGRE NFYQ (m-tenC 14-mer, SEQ ID NO:3); VFQRR MDGQT DFWR (m-tenX 14-mer, SEQ ID NO:4); VFQRR QNGQT DFFR (m-tenR 14-mer, SEQ ID NO:5); VIQHR EDGSL DFQR (m-ang1 14-mer, SEQ ID NO:6); IIQRR EDGSV DFQR (m-ang2 14-mer, SEQ ID NO:7) and VFQKR FNGSV SFFR (m-mfa 14-mer, SEQ ID NO:8).

According to yet another embodiment, the M-tide comprises an amino acid sequence selected from the group consisting of: VYCEI DGSGN GWTVF QKRLD GSVDF KK (m-γ, SEQ ID NO:10); VYCDM NTENG GWTVI QNRQD GSVDF GR (m-β, SEQ ID NO:11); VFCDM TSDGG GWIVF LRRKN GRENF YQ (m-tenC, SEQ ID NO:12); VFCDM ETDGG GWLVF QRRMD GQTDF WR (m-tenX, SEQ ID NO:13); VYCDM TTDGG GWIVF QRRQN GQTDF FR (m-tenR, SEQ ID NO:14); VFCNM DVNGG GWTVI QHRED GSLDF QR (m-ang1, SEQ ID NO: 15); -FYCD MEAGG GWTII QRRED GSVDF QR (m-ang2, SEQ ID NO:16) and VFCDM TTEGG KWTVF QKRFN GSVSF FR (m-mfa, SEQ ID NO:17).

According to yet another embodiment the core haptide comprises an amino acid sequence selected from the group consisting of: KTRWYSMKKTT (peptide preCγ 11-mer, SEQ ID NO: 18); KGPSYSLRSTT (peptide-C-ang1 11-mer, SEQ ID NO:19); KGSGYSLKATTMMIRPADF (peptide-C-ang2, SEQ ID NO:20); KGFEFSVPFTE (peptide-C-tenX 11-mer, SEQ ID NO:21); KGFYYSLKRTE (peptide-C-MFAp 11-mer, SEQ ID NO:22); KGSWYSMRKMS (peptide-C-β 11-mer, SEQ ID NO:23); RGADYSLRAVRMKIR-PLVTQ (peptide-CαE, SEQ ID NO:24) and KGHEHSIQFAEMKLRPSNFR (peptide-CtenC, SEQ ID NO:25).

According to yet another embodiment, the core haptide comprises an amino acid sequence selected from the group consisting of: KTRWYSMKKTTMKIIPFNRL (peptide preCγ SEQ ID NO: 26); KGPSYSLRSTTMMIRPLDF (peptide-Cang1, SEQ ID NO:27); KGFEFSVPFTEMKLR-PRNFR (peptide-CtenX, SEQ ID NO:28); KGFYYSLKR-TEMKIRRA (peptide-Cmfa, SEQ ID NO:29); KGSWYSMRKMSMKIRPFFPQQ (peptide-Cβ, SEQ ID NO:30) and KTRWYSMKKTTMK (peptide preCγ 14-mer, SEQ ID NO:31).

According to yet another embodiment, the chimeric peptide is selected from the group consisting of: KTRW-YSMKKTTMKVFQKRLDGSVDFKK (preCγ-My, SEQ ID NO:32); KGSWYSMRKMSMKVIQNRQDGSVDFGR (Cβ-Mβ, SEQ ID NO:33); KGFEFSVPFTEMKVFQR-RMDGQTDFWR (CtenX-MtenX, SEQ ID NO:34); KGP-SYSLRSTTMMVIQHREDGSLDFQR (Cang1-Mang1, SEQ ID NO:35); KGFYYSLKRTEMKVFQKRFNGSVS-FFR (Cmfa-Mmfa, SEQ ID NO:36); and RGADYSL-RAVRMKLIQQRMDGSLNFNR (CaE-MaE, SEQ ID NO:38).

According to yet another embodiment, the chimeric peptide is selected from the group consisting of: KTRW-YSMKKTTMKXVFQKRLDGSVDFKK (preCγ-Mγ, SEQ ID NO:39); KGSWYSMRKMSMKXVIQNRQDGSVD-FGR (Cβ-Mβ, SEQ ID NO:40); KGFEFSVPFTEMKX-VFQRRMDGQTDFWR (CtenX-MtenX, SEQ ID NO:41); KGPSYSLRSTTMMXVIQHREDGSLDFQR (Cang1-Mang1, SEQ ID NO:42); KGFYYSLKRTEMKX-VFQKRFNGSVSFFR (Cmfa-Mmfa, SEQ ID NO:43); and RGADYSLRAVRMKXLIQQRMDGSLNFNR (CαE-MαE, SEQ ID NO:44), wherein X is a linker, linking the M-tide sequence to the core haptide sequence.

According to yet another embodiment X is a linker, the linker consists of one to fifteen amino acids.

According to yet another embodiment, the chimeric peptide induces cell attachment to a surface to which it is covalently bound, wherein the number of cells attached to the surface is at least 50% greater than the number of cells attached to the surface in the absence of the peptide.

According to yet another aspect, the present invention provides a composition comprising a chimeric peptide comprising an M-tide comprising a sequence that is at least 50% homologous to the amino acid sequence selected from the group consisting of: VFQKR LDGSV DFKK (m-γ 14-mer, SEQ ID NO:1); VIQNR QDGSV DFGR (m-β 14-mer, SEQ ID NO:2) and LIQQR MDGSL NFNR (m-αE 14-mer, SEQ ID NO:37), and a core haptide corresponding to the last 19-21 amino acids of the carboxy termini of the β, γ and αE chains of fibrinogen or from other proteins comprising C-termini that are homologous to said fibrinogen sequences and a pharmaceutically acceptable carrier.

According to one embodiment, the chimeric peptide is derivatized with a tag selected from a fluorescent tag and a radioactive tag.

According to another embodiment, the composition further comprises at least one biological agent. According to yet another embodiment, the at least one biological agent is a therapeutic agent. According to yet another embodiment, the at least one biological agent is selected from the group consisting of vitamins, vitamin derivatives, growth factors, glucocorticosteroids, steroids, antibiotics, toxins, enzymes, enzyme inhibitors, immunomodulators, immunoglobulins and fragments thereof, fatty acid derivatives, polysaccharides, cell receptor binding molecules, anti-inflammatories, nucleic acids, and polynucleotides.

According to yet another embodiment, the chimeric peptide is covalently attached to a solid surface. According to yet another embodiment, the chimeric peptide is covalently attached to the surface of a device, a matrix or a bead.

According to yet another embodiment, the device is a medical device. According to yet another embodiment, the medical device is a medical implant.

According to yet another embodiment, the composition further comprising a plurality of cells selected from the group consisting of mesenchymal cells, parenchymal cells, fibroblasts, endothelial cells, chondrocytes, kidney cells, liver cells, pancreatic cells, thyroid cells, smooth muscle cells and myofibroblasts, wherein the chimeric peptide is covalently attached to the solid surface and is further attached to at least one cell of the plurality of cells.

According to yet another aspect, the present invention provides a polymer composition, comprising a plurality of subunits, each of the subunits comprising at least one chimeric peptide of the invention as well as analogues, derivatives, homologues and active fragments thereof, and further comprising a plurality of linker moieties for covalently linking said plurality of subunits to form the polymer.

According to yet another aspect, the present invention provides methods of using the chimeric peptides of the invention in the treatment of a wound, disease or disorder comprising administering to an individual in need thereof a therapeutically effective amount of a chimeric peptide.

According to yet another aspect, the present invention provides methods of using the chimeric peptides of the invention in the treatment of a wound, disease or disorder comprising implanting into an individual in need thereof a medical implant or device comprising as an active ingredient said chimeric peptides.

According to yet another aspect, the present invention provides methods of using the chimeric peptides of the invention for cell culture and cell separation.

According to yet another aspect, the present invention provides methods of using the chimeric peptides of the invention for fabricating novel cell-containing structures, including biomedical devices.

According to yet another aspect, the present invention provides methods of using the chimeric peptides of the invention for coating natural or synthetic matrices.

According to yet another aspect, the present invention provides methods of using the chimeric peptides of the invention for attracting selected cell types into a biomedical device.

According to yet another embodiment, the present invention provides methods of using the chimeric peptides of the invention for enhancing trans-membrane delivery of chemical cargo, thereby enhancing penetration of the chemical cargo. According to yet another embodiment, the trans-membrane delivery is performed via delivery of nano-particles.

According to yet another embodiment, the chemical cargo comprises at least one gene. According to yet another embodiment, the nano-particles are selected from the group consisting of liposomes, nano-beads and viruses. These and further objects, features and advantages of the present invention will become apparent from the following detailed description and appended claims.

BRIEF DESCRIPTION OF THE DRAWINGS

FIG. 1 is a schematic representation of conserved and homologous m-tide sequences in the γ chain of fibrinogen (A; SEQ ID NOS:10, 45-48) and in various proteins (B; SEQ ID NOS:10-17).

FIG. 2 is a schematic representation of homologous long (17 to 21-mer; A; SEQ ID NO:26, 30, 24, 49, 25, 28, 27, 20 and 29) and short (10-mer; B; SEQ ID NO:18, 23, 21, 19 and 22) haptide sequences in the chains of fibrinogen (upper panels) and other proteins (lower panels).

DETAILED DESCRIPTION OF THE INVENTION

Figure 3A:
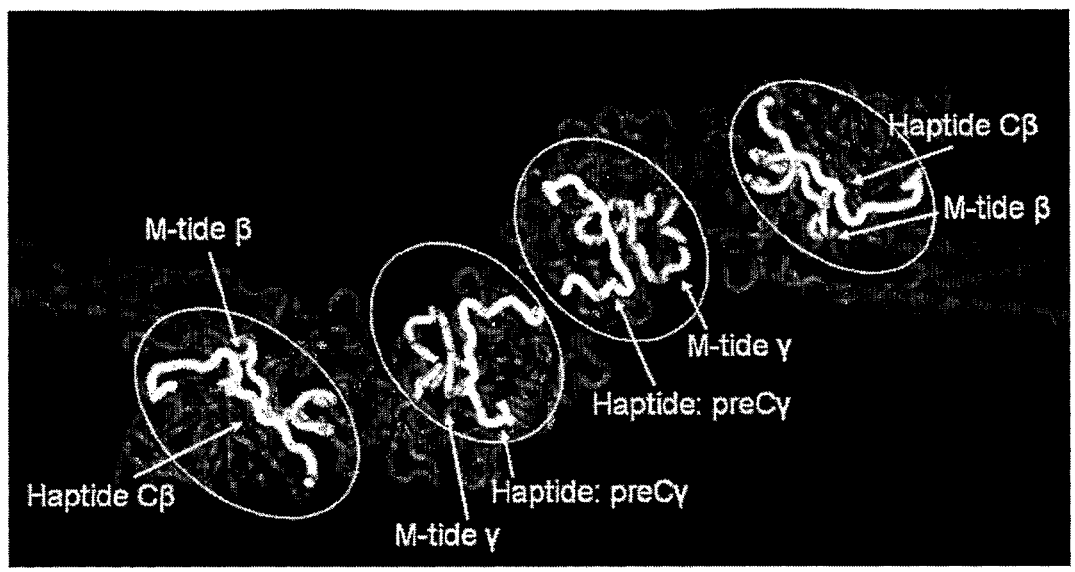
FIG. 3 is a schematic presentation of the 3-D organization of m-tides and haptides within various domains of fibrinogen (A), a representation of conserved and homologous M-tide sequences in the γ chain of fibrinogen (B) and in various proteins (C).

The present invention is directed to cell attachment synthetic peptides, also designated herein 'chimeric peptides', comprising an M-tide and a corresponding core haptide. Also provided are uses for these sequences in vivo as well as in vitro. For example, the peptides of the invention have many potential medical uses, including but not limited to therapeutic and diagnostic uses. Advantageously, the synthetic peptide of the invention comprise shorter peptides that are homologous to regions of large proteins, such as fibrin(ogen), yet retain certain desired properties of the entire molecule, such as the ability to induce and enhance cell adhesiveness. Surprisingly, the synthetic chimeric peptides of the invention do not posses any linear sequence homology to known native peptides. As exemplified hereinbelow, the unique features of the chimeric peptides of the present invention render them suitable for applications in diverse fields including cell manipulation, wound healing and tissue engineering.

The term "fibrin(ogen)" is known in the art and denotes either fibrinogen or fibrin or a mixture of fibrin and fibrinogen, and is referred to herein according to this definition.

Hereinafter, the term "biologically active" refers to molecules, or complexes thereof, which are capable of eliciting an effect in a biological system.

Hereinafter, the term "fragment" refers to a portion of a molecule or a complex thereof, in which the portion includes substantially less than the entirety of the molecule or the complex thereof.

The term "amino acid" as used herein refers to compounds which have an amino terminus and carboxy terminus. Amino acids may include natural, biosynthetic and synthetically derived α-amino acids, such as amino-isobutyric acid, norleucine, norvaline, homocysteine and homoserine, β-Alanine and γ-amino butyric acid, which are merely examples of 1,3 and 1,4-amino acids, and many others are well known in the art.

As used herein "peptide" indicates a sequence of amino acids linked by peptide bonds. The peptide analogs of this invention comprise a sequence of amino acids of 24 to 27 amino acid residues, each residue being characterized by having an amino and a carboxy terminus.

As used herein, the term "haptotactic peptide(s)" refers to amino-acid sequences or analogues or derivatives or peptidomimetics thereof, which are capable of eliciting attachment responses from cells, whereby the attachment of the cells in the presence of the haptotactic molecule is at least 50% greater than that in the absence thereof.

Hereinafter, the term "wound-healing cells" refers to those cells, which promote healing of a wound, including, but not limited to, fibroblasts, smooth muscle endothelial cells, osteoblasts and chondrocytes.

Preferred Modes for Carrying Out the Invention

Within the scope of the present invention it is to be understood that the chimeric peptides disclosed are preferred embodiments and intended to be construed as encompassing shorter active fragments thereof as well as homologs, derivatives and analogs, as defined hereinbelow.

The inventors of the present invention previously discovered a family of peptides, derived from the C-termini of β and γ chains of fibrinogen and its extended alpha chain (αE) (FIG. 2; U.S. Pat. Nos. 7,122,620 and 7,148,190). These peptides, also termed herein "haptides", are about 10-25 amino-acids long, typically, 17-21 amino-acids long, capable of inducing cell attachment (haptotaxis) and have the ability to enhance cellular internalization of different substances.

A voluminous literature exists which describes the binding of fibrinogen (γ400-411) to platelets through the GPIIb/IIIa receptor and the aggregation activity of the new amino Bβ15-42 terminus that is exposed after release of fibrinopeptide B. The preCγ haptide precedes the terminal sequence of the gamma chain. Fibrinogen fragment E was reported to exhibit angiogenic properties and to inhibit endothelial cell migration in a Boyden chamber chemotactic assay. The larger fragment D was reported to cause detachment of cultured endothelial cells from the extracellular matrix (ECM) substratum in a concentration and time dependent process.

Isolated constituent chains of fibrinogen (Aα1, Aα2 and Bβ) released upon activation of fibrinogen by thrombin were observed to stimulate fibroblast proliferation by 23 31% above controls, whereas isolated γ chain had no effect. Human polymorphonuclear leukocytes (PMN) were shown to bind to fibrin(ogen) coated surfaces via a type 3 (CD11b/CD 18) complement receptor homologous to the GPIIb/IIIa receptor through a decamer of the γ chain carboxy terminus (LGGAKQAGDV; SEQ ID NO: 9). Vasoactive peptides were identified corresponding to residues 43. The biological activities of fibrinogen breakdown products have been investigated, but the cellular activity seemed to be widely variable.

Functional peptide sequences previously have been disclosed on the γ-chain, including sites involved in platelet binding (γ 400-411), leukocyte adhesion (γ 396-411), factor XIII-crosslinking sites (γ 398, γ 407), a polymerization region (γ 374-395), and fibroblast adhesion region (γ 374-394). Thus, fibrinogen interactions with platelets and cells have been documented by a number of workers.

Fibrinogen chains β and γ encompass other conserved regions that are highly preserved between different species and also are homologous to sequences in different proteins containing the haptides sequences. The addresses of these conserved homologous sequences in human fibrinogen are 206-232 in the γ chain and 268-294 in the β chain. Homologous sequences also appear in all members of the protein family having the haptide containing domain FRED in their C-terminus. 3D visualization of all these FRED containing proteins show that this conserved regions in the middle of the chains are folded and aligned so that part of it forms a beta sheet with part of the relevant "haptides" sequences. We termed this family of homologous sequences that naturally form beta sheets with the haptide sequences "full length M-tides". Thus, in the native fibrinogen three-dimensional organization there are M-tides β and γ sequences that co-locate with the relevant haptides Cβ and preCγ, as shown in FIG. 3.

Without wishing to be bound by any theory or mechanism, the inventors of the present invention speculate that the stability of the new synthetic chimeric peptide is based on the fact that the part of the M-tide sequence in the natural protein folding, always forms a beta sheet with part of haptide.

It is now disclosed that novel family of homologous peptides (M-tides) that are equivalent to sequences within fibrinogen and also contain amino acid sequences which are homologous to portions of the carboxy termini of fibrinogen chains, when linked to haptides, form chimeric peptides that have the ability to induce and enhance cell attachment. Moreover, the chimeric peptides exhibit exceptionally high stability.

The stability of the chimeric peptides may be attributed to the 3-D conformation of these two sequences in the entire protein from which they are derived. The haptide and M-tide are co-located as a "beta sheet" but are far away from each other on a linear sequence of the molecule (FIG. 3). As a matter of fact, the chimeric peptides of the invention are composed of fragments of the beta sheet, one fragment corresponds to a haptide and the other is a new short peptide that when combined to the known haptides, stabilizes the resulting synthetic, chimeric, peptide.

Certain 14-mer M-tides included in the chimeric peptides, according to the invention, were synthesized as individual peptides, including the following:

```
VFQKR LDGSV DFKK;   (m-γ 14-mer, SEQ ID NO: 1)

VIQNR QDGSV DFGR;   (m-β 14-mer, SEQ ID NO: 2)

VFLRR KNGRE NFYQ;   (m-tenC 14-mer, SEQ ID NO: 3)

VFQRR MDGQT DFWR;   (m-tenX 14-mer, SEQ ID NO: 4)

VFQRR QNGQT DFFR;   (m-tenR 14-mer, SEQ ID NO: 5)

VIQHR EDGSL DFQR;   (m-ang1 14-mer, SEQ ID NO: 6)

IIQRR EDGSV DFQR;   (m-ang2 14-mer, SEQ ID NO: 7)
and

VFQKR FNGSV SFFR.   (m-mfa 14-mer, SEQ ID NO: 8)

Additional 22-mer M-tides according to the
invention include:
VYCEI DGSGN GWTVF  (m-γ SEQ ID NO: 10)
QKRLD GSVDF KK;

VYCDM NTENG GWTVI  (m-β, SEQ ID NO: 11)
QNRQD GSVDF GR;

VFCDM TSDGG GWIVF  (m-tenC, SEQ ID NO: 12)
LRRKN GRENF YQ;
```

-continued

```
VFCDM ETDGG GWLVF   (m-tenX, SEQ ID NO: 13)
QRRMD GQTDF WR;

VYCDM TTDGG GWIVF   (m-tenR, SEQ ID NO: 14)
QRRQN GQTDF FR;

VFCNM DVNGG GWTVI   (m-ang1, SEQ ID NO: 15)
QHRED GSLDF QR;

-FYCD MEAGG GWTII   (m-ang2, SEQ ID NO: 16)
QRRED GSVDF QR;
and

VFCDM TTEGG KWTVF   (m-mfa, SEQ ID NO: 17)
QKRFN GSVSF FR.
```

Further chimeric peptides according to the invention were synthesized as individual peptides, namely:

```
KTRWYSMKKTTMKVFQKRLD   (preCγ-Mγ, SEQ ID NO: 32)
GSVDFKK;

KGSWYSMRKMSMKVIQNRQD   (Cβ-Mβ, SEQ ID NO: 33)
GSVDFGR;

KGFEFSVPFTEMKVFQRRMD   (CtenX-MtenX, SEQ ID NO: 34)
GQTDFWR;

KGPSYSLRSTTMMVIQHRED   (Cang1-Mang1, SEQ ID NO: 35)
GSLDFQR;

KGFYYSLKRTEMKVFQKRFN   (Cmfa-Mmfa, SEQ ID NO: 36)
GSVSFFR;
and

RGADYSLRAVRMKLIQQRMD   (CαE-MαE, SEQ ID NO: 38)
GSLNFNR.
```

Alternatively, the chimeric peptides comprise a linker, X, linking the M-tide to the haptide as set forth in SEQ ID NOS:39-44. The linker X may be any suitable linker for linking the M-tide to the haptide. The two sequences may be linked through a peptide bond, such that no linker is introduced between the linked sequences. However, a linker may be added for strengthening the combined peptides, for example by assisting or enabling the folding of the combined peptidic sequence into a stable beta-sheet.

It should be noted that conservative replacements of the amino acid residues of the aforementioned chimeric peptide sequences are also encompassed within the scope of the present invention, as is well known in the art.

Moreover, the aforementioned sequences themselves, as well as analogs or derivatives comprising an additional spacer moiety or rearrangement for proper geometrical configuration, are also disclosed herein as M-tides and chimeric peptides of the present invention. It is intended to be understood that all known peptides encompassed within the aforementioned sequences are explicitly excluded, including but not limited to the known haptides, specifically, the following 11-mer haptides:

```
KTRWYSMKKTT;   (peptide preCγ 11-mer, SEQ ID NO: 18)

KGPSYSLRSTT;   (peptide-C-ang1 11-mer, SEQ ID NO: 19)

KGFEFSVPFTE;   (peptide-C-tenX 11-mer, SEQ ID NO: 21)

KGFYYSLKRTE;   (peptide-C-mfap 11-mer, SEQ ID NO: 22)

KGSWYSMRKMS;   (peptide-C-β 11-mer, SEQ ID NO: 23)
``` and the following 17 to 21-mer haptides:

```
KGSGY SLKAT TMMIR PADF;    (peptide-C-ang2,
                            SEQ ID NO: 20)

RGADY SLRAV RMKIR PLVTQ;   (peptide-C-αE,
                            SEQ ID NO: 24)

KGHEH SIQFA EMKLR PSNFR;   (peptide-CtenC,
                            SEQ ID NO: 25)

KTRWY SMKKT TMKII PFNRL;   (peptide preCγ
                            SEQ ID NO: 26)

KGPSY SLRST TMMIR PLDF;    (peptide-C-ang1,
                            SEQ ID NO: 27)

KGFEF SVPFT EMKLR PRNFR;   (peptide-C-tenX,
                            SEQ ID NO: 28)

KGFYY SLKRT EMKIR RA;      (peptide-C-mfa,
                            SEQ ID NO: 29)
and KGSWY SMRKM SMKIR PFFPQ Q  (peptide-C-β,
                            SEQ ID NO: 30)
```

The M-tides discovered herein are not only homologous to portions of fibrinogen, but rather are homologous to portions of other proteins having sequence homology to the haptide sequences in the C-termini of β and γ chains of fibrinogen and its extended alpha chain (αE) (e.g. SEQ ID NOS: 3-8 and 12-17; FIG. 1). These proteins include, for example, angiopoietin 1 (ang1) and angiopoietin 2 (ang2) (MW about 130 kDa). Ang-1 and ang-2 factors contain the haptotactic motif shared by fibrinogen Cβ and preCγ (the degree of homology having a statistical significance of p<0.001). These factors are secreted by cells to modulate vasculature formation in normal and cancer tissue. While ang1 serves as a stimulator of capillary development, ang2 is an inhibitor thereof. The receptors for these angiopoietins have been identified as the tyrosine kinase receptors Tie-1- and Tie-2.

Another protein family found to include M-tide sequences is the family of tenascins. These proteins contain a fibrinogen-like domain and a sequence homologous to Cβ (FIGS. 1 and 2). Tenascins have been associated with the growth of neurons, but are ubiquitous and may serve other developmental functions, including binding to and modulating membrane sodium channels. Cell receptors identified to date for tenascins include integrins $\alpha_8\beta_1$ and $\alpha_9\beta_1$. Some tenascins are organized as hexamers.

Microfibril-associated glycoprotein-4 ("MFAP4") was also found to include M-tide sequences. In addition, the C-terminus of MFAP4 (C-mfa) was found homologous to fibrin related haptides. This protein relates to the Smith-Magenis syndrome (SMS), a clinically recognizable multiple congenital anomaly/mental retardation syndrome associated with deletion of chromosome 17p11.2. The gene encoding human MFAP4 has been mapped to the SMS region that has a fibrinogen-like domain. A full-length cDNA corresponding to the MFAP4 gene contains a coding region of 255 amino acids. Deletion of the MFAP4 gene locus in SMS patients has been considered in the pathogenesis of this genetic disorder.

The chimeric peptides of the present invention are contemplated for many different uses, including but not limited to the treatment of a wound bed. Additional uses of the chimeric peptides of the present invention include, but are not limited to, the separation of different types of cells from mixed cell cultures, the implantation of peptide-coated prosthetic devices, the identification and analysis of cell receptor mechanisms, the design of peptide-derivatized drugs to augment drug delivery and for diagnostic purposes. Furthermore, as explained in greater detail below, the chimeric peptides of the present invention or their DNA or RNA sequences can also be used as tools for biological analysis and for further research and development. In addition, the chimeric peptides of the invention may be used for enhancing the penetration and internalization of therapeutic moieties, including therapeutic moieties incorporated within or attached to liposomes, into cells.

The peptides of the invention may be synthesized and covalently attached to Sepharose beads, to form SB-peptide, as exemplified hereinbelow. Upon incubation with cultured cells, it was discovered that the chimeric peptides are potent for cell binding, with potency equivalent to that of the parent fibrinogen molecule (entire protein). The chimeric peptide exhibited significantly long shelf life and also improved haptotaxis in comparison to haptides.

The principles and operation of the invention, using peptidic amino acid sequences of fibrin and homologous sequences according to the present invention may be better understood with reference to the following non-limiting illustrative examples.

EXAMPLES

Haptotaxis Assay

The peptides of the invention were bound to CNBr activated Sepharose beads (SB) following the manufacturer's coupling procedure and stored in 4° C. SB were coated, through covalent bonds, to peptides yielding a final concentration of 6 or 12 mg peptide/ml SB.

Figure 4A:
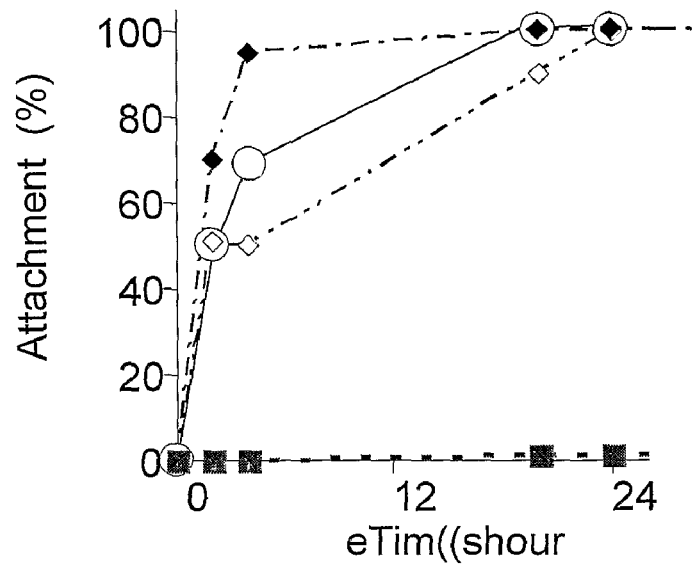
FIG. 4 presents attachment of foreskin fibroblasts (FF) to cell structures comprising in-tides, haptides or chimeric peptides coupled to Sepharose beads.
Figure 4B:
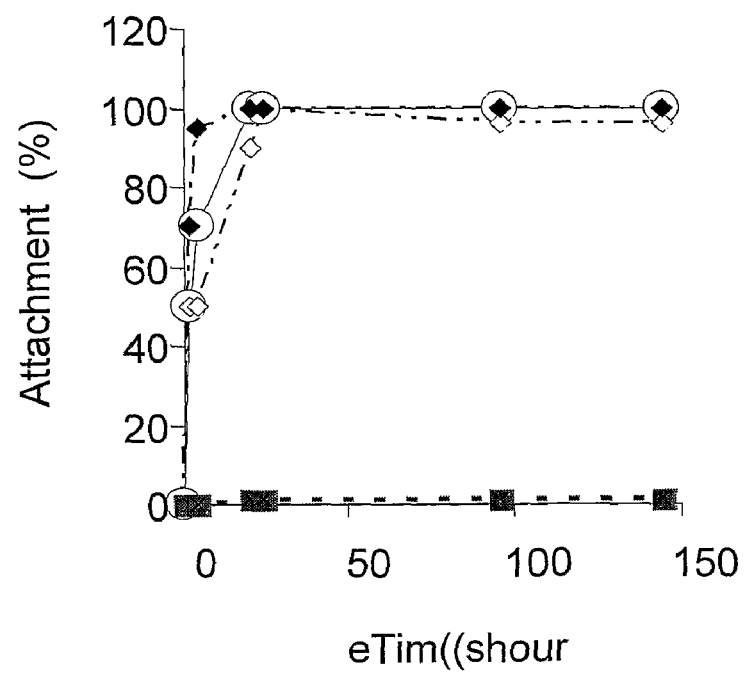
Figure 4C:
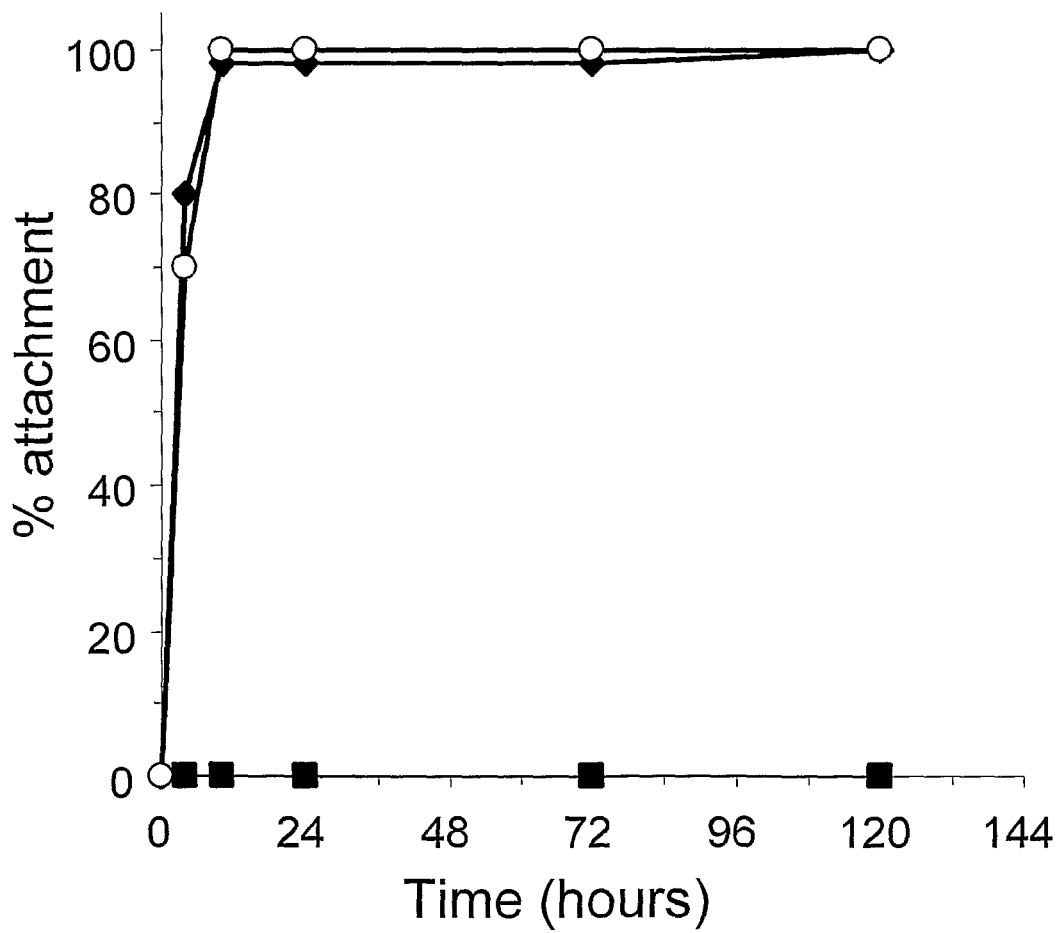
Figure 5A:
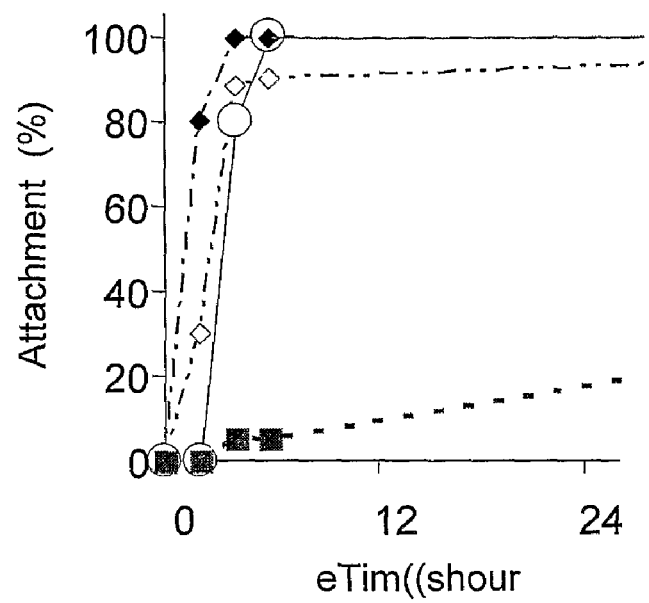
FIG. 5 shows attachment of bovine aortic endothelial cells (BAEC) to cell structures comprising m-tides, haptides or chimeric peptides coupled to Sepharose beads.
Figure 5B:
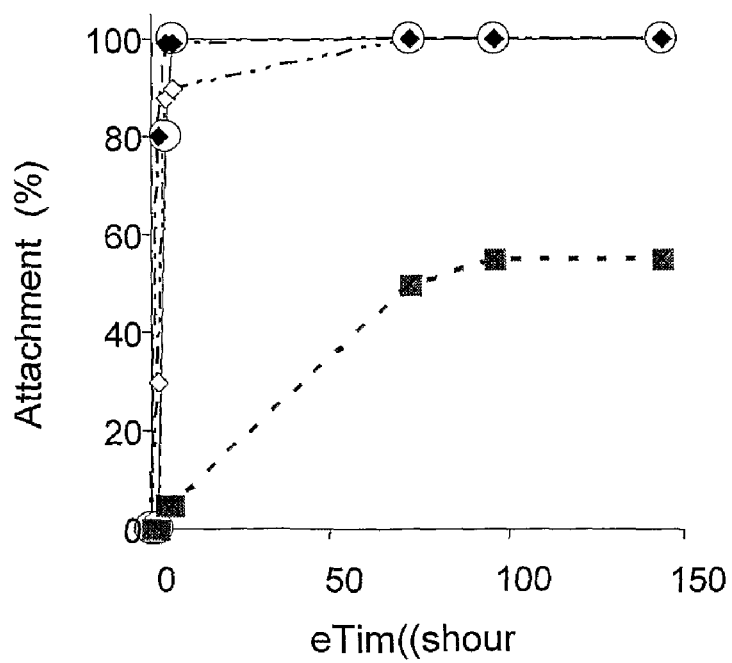
Figure 5C:
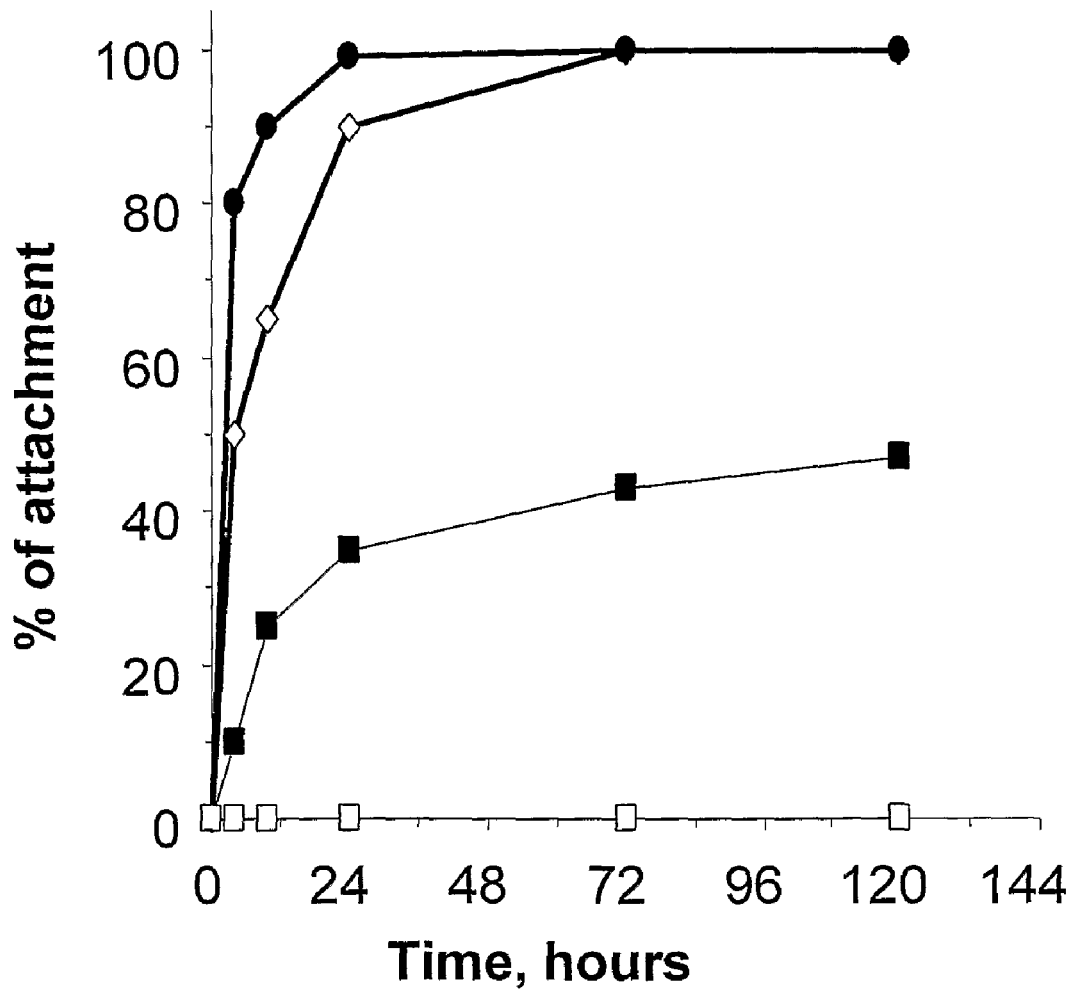

At least two cell types were tested: foreskin fibroblasts (FF; e.g. FIG. 4) and bovine aortic endothelial cells (BAEC; e.g. FIG. 5) as previously described (U.S. Pat. Nos. 7,122,620 and 7,148,190). Briefly, cells were grown in 12 well plates to sub-confluence (until cells covered about ⅔ of a plate's surface). Approximately 20-150 μl of suspended (50% v/v) SB-peptide or SB-protein (typically about 300 SB-peptide—but not less than 200, per well) were added to 6-24 well plates with near confluent cell cultures and dispersed by gentle shaking for 1 min. The plates were then incubated for up to 4 days. At different time points, the number of SB tethered to cells was counted with an inverted phase microscope. The ratio between the number of SB attached to the cells in each well, was calculated relative to the total number of SB seeded. Only SB coated with haptotactic materials became attached to the cell layer, ultimately to be engulfed by cells and tethered to the plate. Uncoated SB or SB coated with a neutral molecule such as BSA (control), none of the SB became attached to cells on the plate.

For the M-tide, previous data showed that concentrations lower than 12 mg/ml are not sufficient for significant Haptotaxis. Therefore only the higher dose of the peptide was tested, which resulted in a weak haptotatic effect for some M-tide sequences.

Ageing Test

For testing peptides ageing of the peptides, the SB-peptides were incubated in room temperatures for different time periods in a coupling buffer comprising azide (to prevent contamination). At each time point, samples were transferred to Eppendorf tubes and haptotaxis was tested in accordance with the Haptotaxis assay.

Example 1

Haptotaxis

Haptotaxis was examined with the following peptides-SB structures:
1. SB-M-tide: SB coupled to an M-tide homologous to a fragment of the γ chain of fibrinogen (SEQ ID NO:1), at a concentration of 6 mg peptide per 1 ml of SB (cross in a grey box, FIGS. 4A-B and 5A-B; black square, FIGS. 4C and 5C).
2. SB-C-M-tide: SB coupled to a chimeric peptide (KTRWYSMKKTT MKVFQKRLDGSVDFKK, preCγ-Mγ; SEQ ID NO:32), comprising part of the M-tide of SEQ ID NO: 1 and the preCγ haptide, which is derived from the C-terminus of the γ chain of fibrinogen (KTRWYSMKKTTMK; SEQ ID NO: 31) and devoid of a linker, at a concentration of at a concentration of 12 mg peptide per 1 ml of SB (black diamond; FIGS. 4A-B and 5A-B) or 6 mg peptide per 1 ml of SB (white diamond, FIGS. 4A-C and 5A-C).
3. SB-preCγ: SB coupled to the haptide set forth in SEQ ID NO:31, at a concentration of 6 mg peptide per 1 ml of SB (white circles, FIGS. 4A-C and 5A-C).

The results show that cell attachment to SB covered with the chimeric peptides is higher than attachment to SB covered only with haptides. Thus, the data clearly indicates that cellular attachment to haptides is improved when the haptide is incorporated within the chimeric peptides of the invention. As detailed above and exemplified herein, cell attachment to SB covered with M-tide alone is poor. Thus, the M-tide/haptide combination, presented by the chimeric peptides of the invention, is advantageous in terms of cell attachment, over each one of the components (haptide or M-tide) alone.

Example 2

The Effect of Ageing on Haptotaxis

The rate of attachment of the chimeric peptides of the invention to cells (Haptotaxis assay) was examined with peptides-SB structures that were stored at room temperature for different time points from 24 hours to 21 days (FIGS. 6-8) in BAEC (FIGS. 6 and 7) or FF (FIG. 8). Aged structures were added to 6-24 well plates with near confluent cell cultures, and haptotaxis was followed up in accordance with the Haptotaxis assay.

Figure 6A:
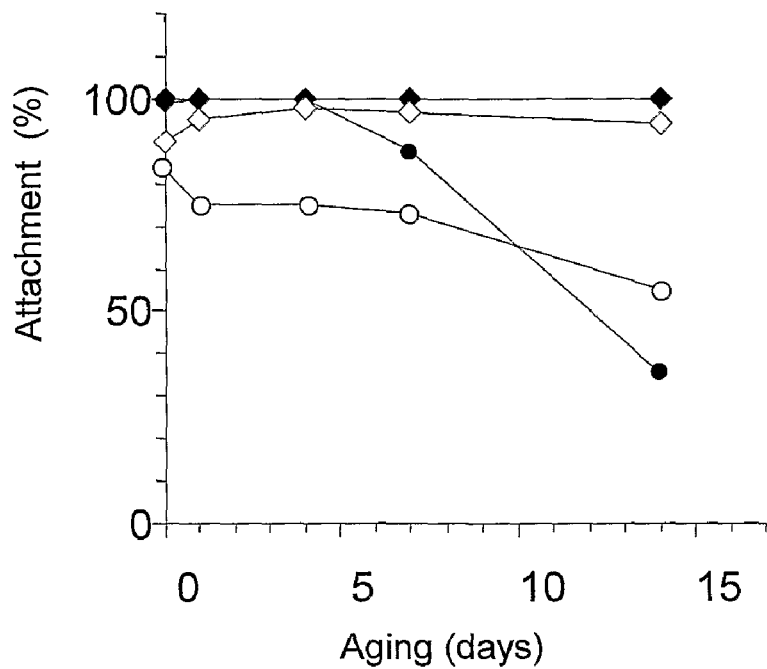
FIG. 6 exhibits the effect of ageing peptides (m-tides, haptides or chimeric peptides coupled to Sepharose beads stored at RT for 24 hours before exposure to cells) on haptotaxis of bovine aortic endothelial cells (A) and foreskin fibroblasts (B).
Figure 6B:
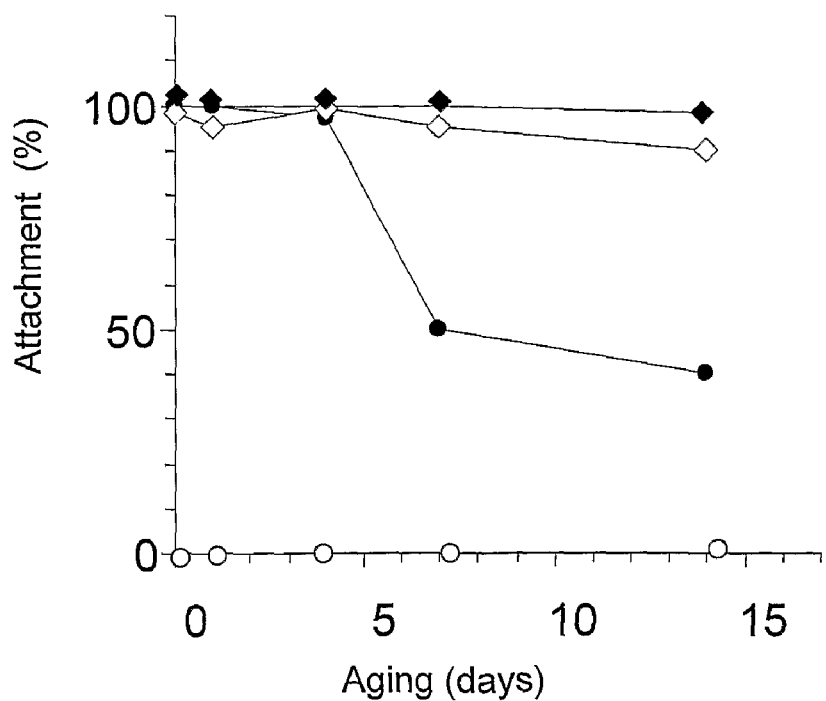
Figure 7A:
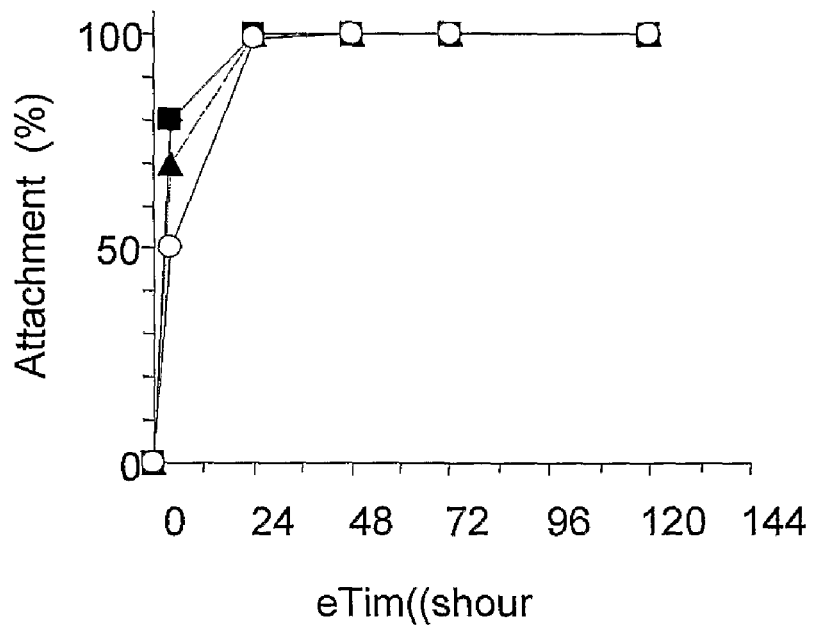
FIG. 7 demonstrates the effect of an ageing chimeric peptide (KTRWYSMKKTTMKVFQKRLDGSVDFKK, preCγ-Mγ; SEQ ID NO:32), M-tide haptide or fibrinogen, coupled to Sepharose beads at 6 and 12 mg peptide/ml beads on haptotaxis of bovine aortic endothelial cells.
Figure 7B:
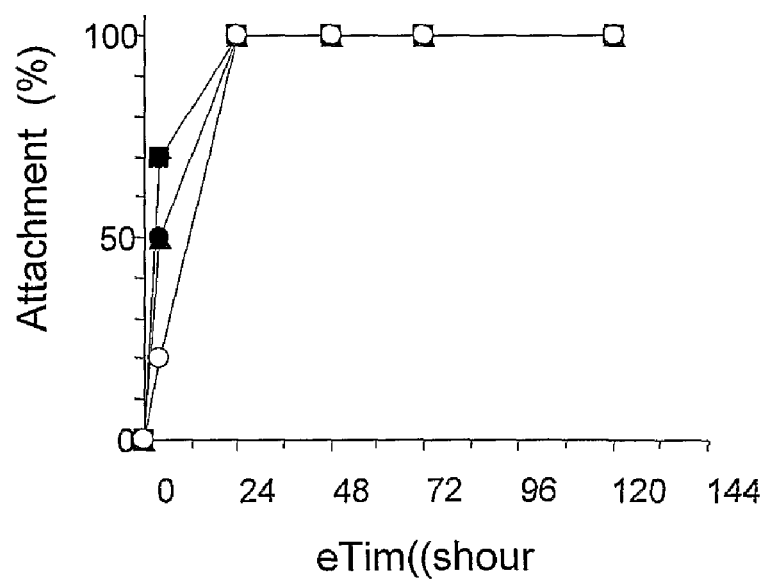
Figure 7C:
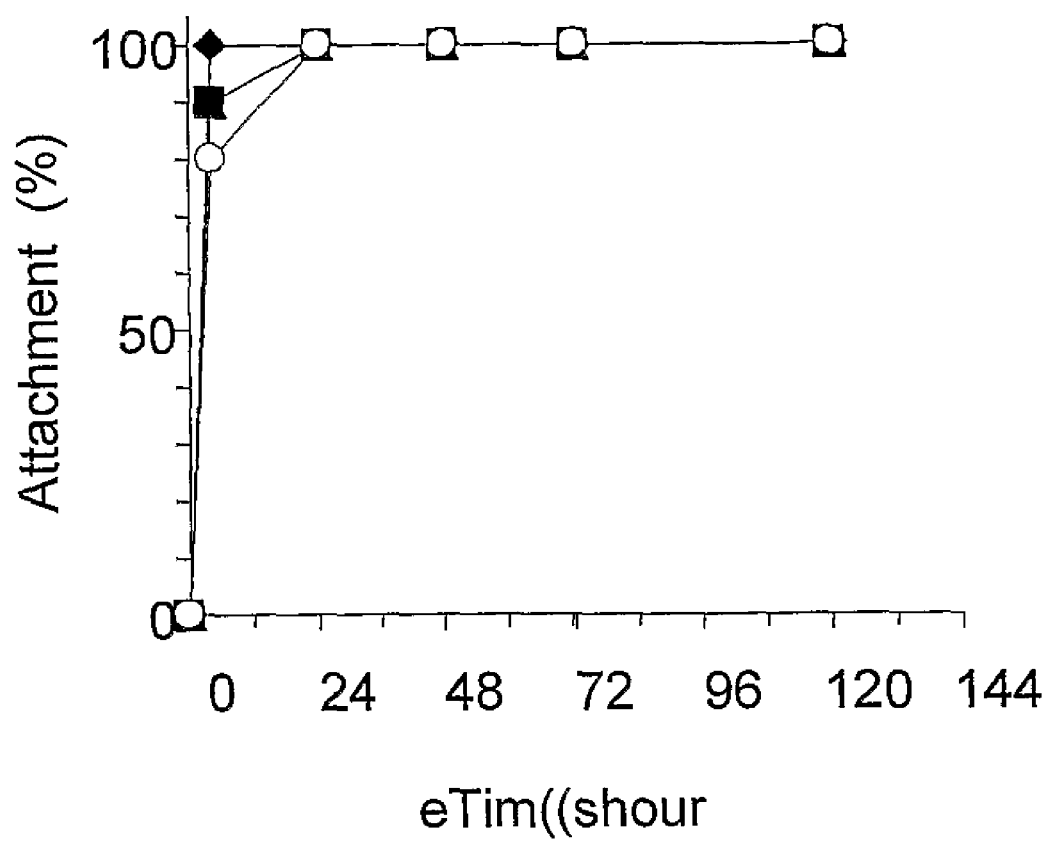
Figure 7D:
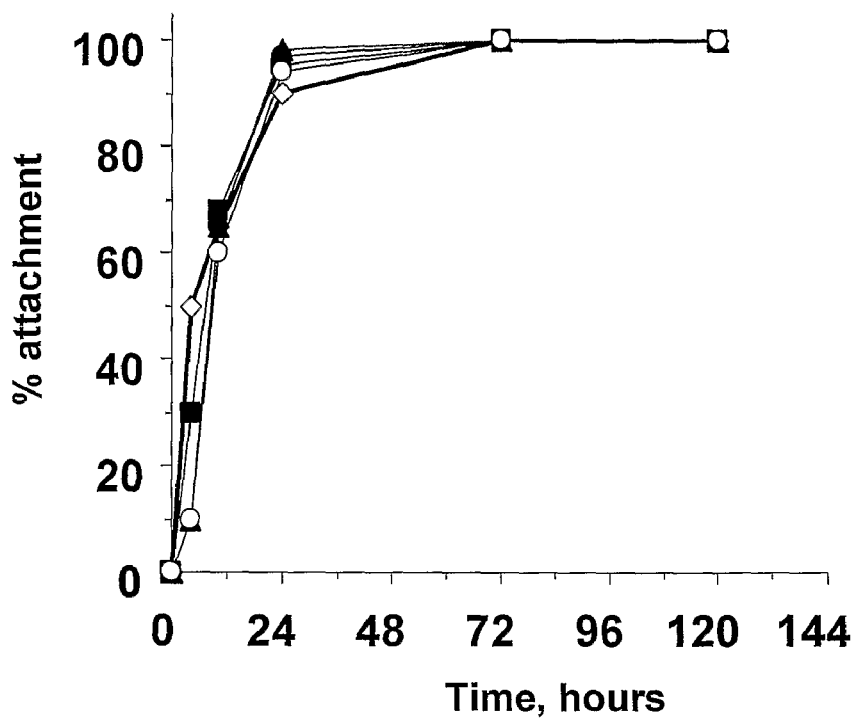
Figure 8A:
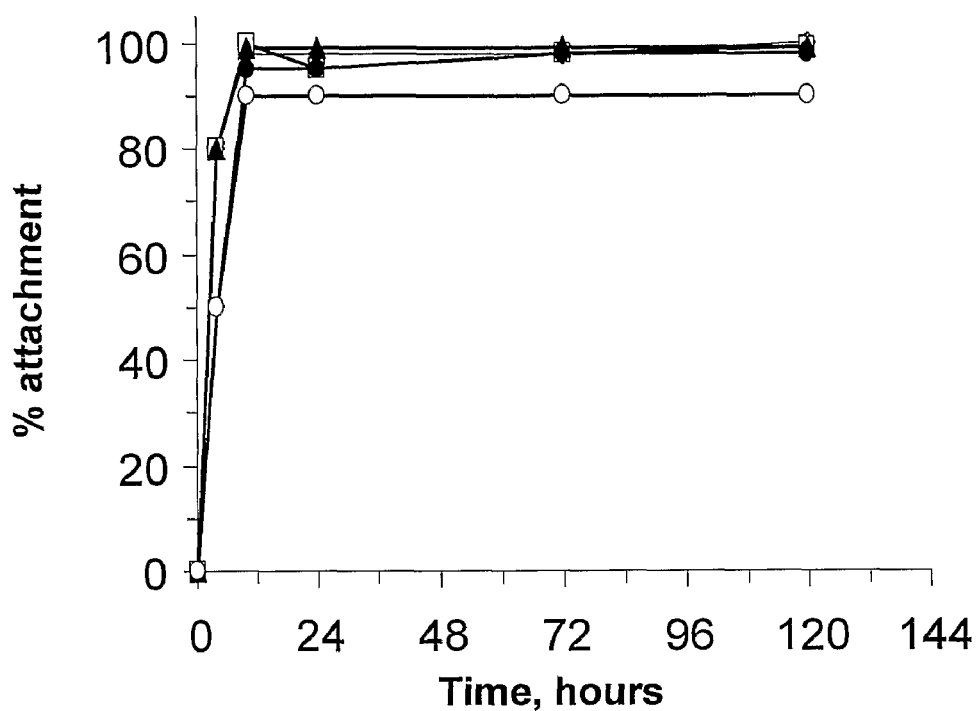
FIG. 8 exhibits the effect of ageing peptides (m-tides, haptides or chimeric peptides coupled to Sepharose beads stored at RT for 24 hours before exposure to cells) on haptotaxis of foreskin fibroblasts.
Figure 8B:
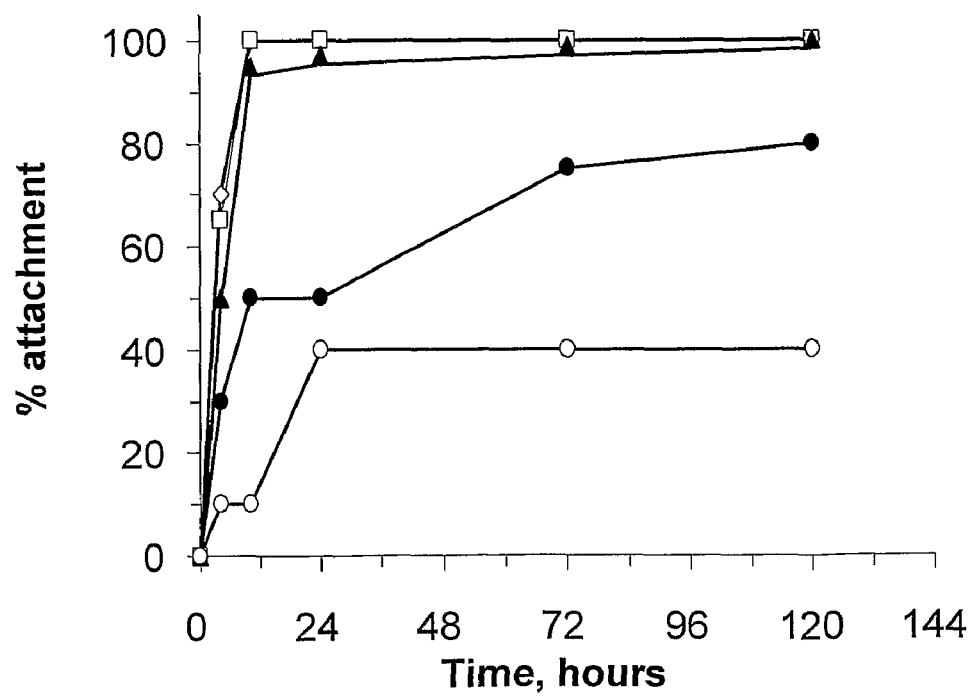

The following aged peptides-SB structures were examined:
1. SB-m-tide-12: SB coupled to an M-tide, aged for 24 hrs in BAEC and FF (FIG. 6A and FIG. 6B, respectively; white circles), derived from the γ chain of fibrinogen (SEQ ID NO:1), at a concentration of 12 mg peptide per 1 ml of SB.
2. SB-C-m-tide: SB coupled to the chimeric peptide set forth in SEQ ID NO:32, at a concentration of 12 mg peptide per 1 ml of SB, aged for 24 hrs in BAEC and FF (black diamond; FIGS. 6A-B, respectively). The chimeric peptide aged for 24 hrs was also exposed at a concentration of 6 mg peptide per 1 ml of SB, to BAEC and FF (white/empty diamond; FIGS. 6A-B, respectively). In addition, the chimeric peptide at a concentration of 6 mg peptide per 1 ml of SB (FIGS. 7A and 7D) or 12 mg peptide per 1 ml of SB (FIG. 7B), following aging for 1 day (FIGS. 7A, 7B and 7D; black square), 4 days (black triangle; FIG. 7D), 6 days (black triangle; FIGS. 7A and 7B), 7 days (black circle; FIG. 7D), 14 days (black circle; FIGS. 7A and 7B and white circle; FIG. 7D) and 21 days (white circles; FIGS. 7A and 7B) was exposed to BAEC. Also shown is a control sample of the chimeric peptide, which was maintained at 4° C., i.e. not exposed to room temperature (empty diamonds; FIGS. 7A, 7B and 7D).

Furthermore, the chimeric peptide at a concentration of 6 mg peptide per 1 ml of SB was exposed to FF (FIG. 8A) following aging for 1 day (black square), 4 days (black triangle), 7 days (black circle) and 14 days (white circle). Also shown is a control sample of the chimeric peptide, which was maintained at 4° C., i.e. not exposed to room temperature (empty diamonds).

Figure 7E:
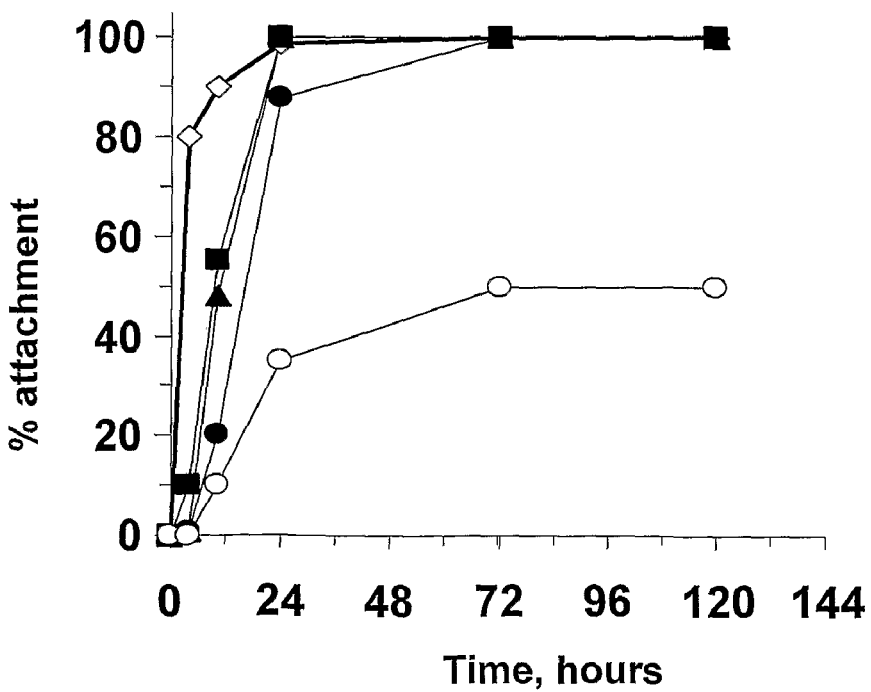

3. SB-preCγ: SB coupled to the haptide set forth in SEQ ID NO:31, at a concentration of 6 mg peptide per 1 ml of SB, aged for 24 hrs in BAEC and FF (black circles; FIGS. 6A-B, respectively). In addition, FIG. 7E shows SB coupled to the haptide set forth in SEQ ID NO:31 (SB-preCγ), at a concentration of 6 mg peptide per 1 ml of SB, aged for 1 day (black square), 4 days (black triangle), 7 days (black circle) and 14 days (white circles) prior to exposure to BAEC. Also shown is a control sample (empty diamond), which was maintained at 4° C. (i.e. not exposed to room temperature).

Furthermore, SB coupled to the haptide set forth in SEQ ID NO:31 (SB-preCγ), at a concentration of 6 mg peptide per 1 ml of SB, was exposed to FF (FIG. 8B) after aging for 1 day (black square), 4 days (black triangle), 7 days (black circle) and 14 days (white circles). Also shown is a control sample (empty diamond), which was maintained at 4° C. (i.e. not exposed to room temperature).

4. Haptotaxis was also measured with SB bound to high concentration of fibrinogen (24 mg protein/ml SB; FIG. 7C). Percentage of attachment was measured with structure stored (aged) for 1 day (black square), 6 days (black triangle), 14 days (black circle) and 21 days (white circles) prior to exposure to BAEC. Also shown is a control sample (empty diamond), which was maintained at 4° C. (i.e. not exposed to room temperature). Aged structures were added to 6-24 well plates with near confluent cell cultures, and haptotaxis was determined in accordance with the Haptotaxis assay.

The results show that cellular attachment to aged SB covered with the haptides alone, decreases with time (e.g. FIG. 7E), while cellular attachment to the chimeric peptides of the invention aged for days to weeks at room temperature, is maintained. Accordingly, the chimeric peptides exhibit enhanced stability with respect to the haptide alone, which may reflect on their prolonged shelf life relative to shelf life of haptides alone.

Example 3

Toxicity Assessment

Figure 9A:
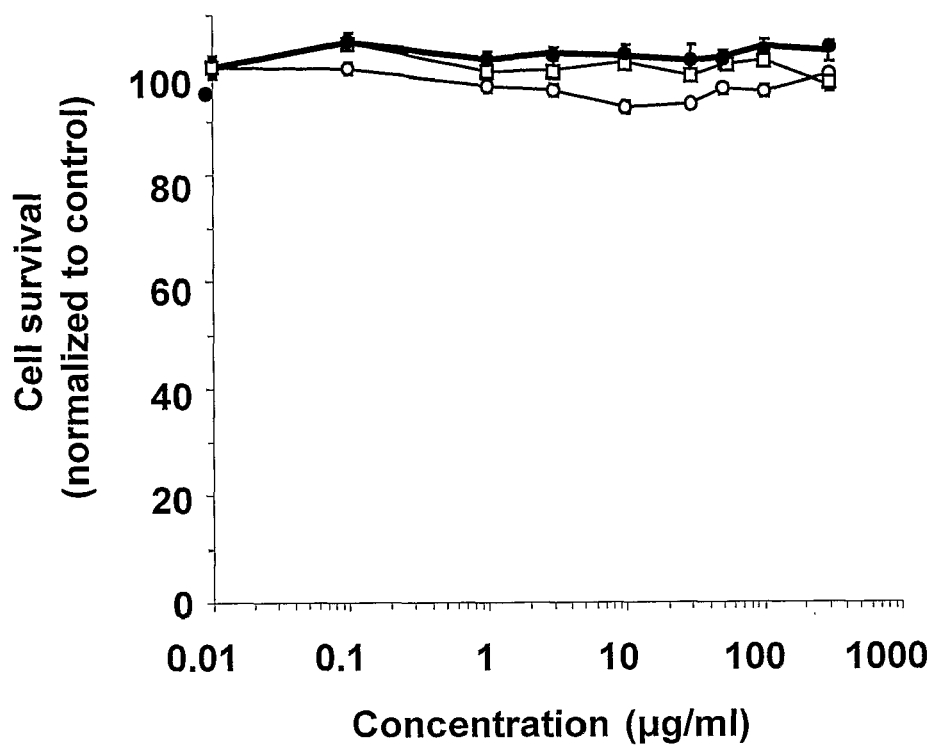
FIG. 9 shows the dose response of cultures BAEC (A) and FF (B) upon exposure to a wide range of concentrations of haptides, M-tides and the chimeric peptide for 48 hours.
Figure 9B:
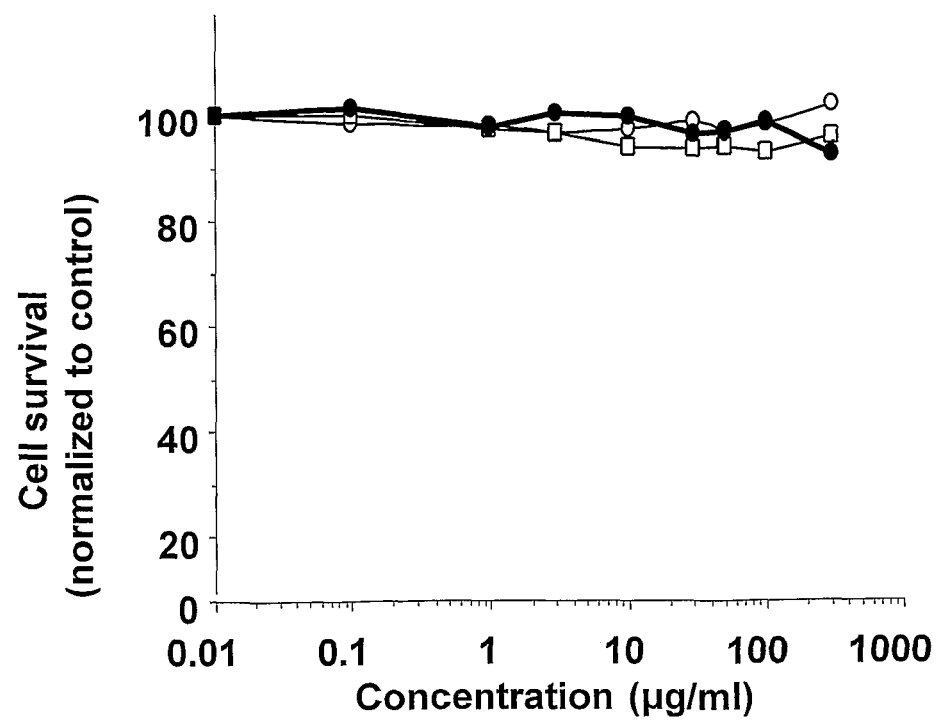
Figure 10:
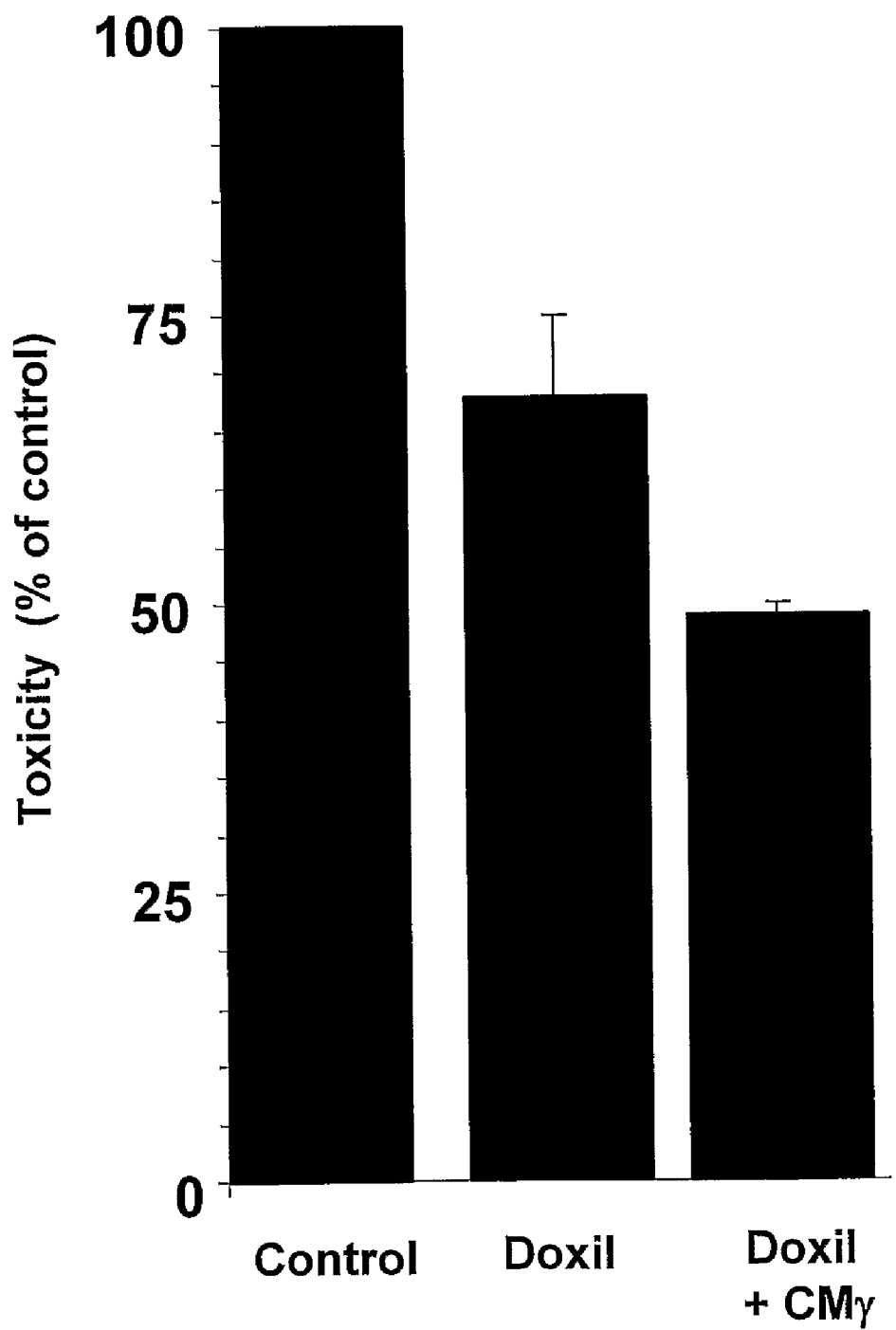
FIG. 10 exhibits the toxicity of doxorubicin liopomes (Doxil) formulation when exposed to FF in the absence or presence of the chimeric-γ peptide (100 µg/ml).

The chimeric peptides of the invention and the peptides from which they are derived were found safe, non-toxic, to normal cells such endothelial cells (BAEC; FIG. 9a) and fibroblasts (FF; FIG. 9B). Cells incubated with increasing concentrations (up to 1,000 ng/ml) of the chimeric peptide (black square), the haptide alone (white/empty circle) or the M-tide alone (white/empty square), maintained 100% survival. Cell survival was measured following 48 hours of exposure to the peptides.

Example 4

Cellular Intake

The potential of the chimeric peptide of enhance the intake of nanoparticles, such as, liposomal formulations, loaded with different drugs or chemicals, viruses and gene carrying vectors, was demonstrated as shown in FIG. 9.

The chimeric peptide of the present invention was shown to penetrate into cells and enhance the intake of nanoparticles in the form of doxorubicin liposome (Doxil) formulation. FIG. 9 shows the toxicity of Doxil formulation upon exposure to FF the chimeric-y peptide (100 μg/ml) with Doxil or Doxil alone. The data shows that the chimeric peptide enhances the toxicity of Doxil towards the tested cells. This effect is attributed to the peptide-enhanced penetration of the liposomes into the cells.

Example 5

Cell Structures Comprising M-Tides and Chimeric Peptides

The chimeric peptides of the present invention may be used for constructing structured cell systems, for example as for tissue engineering. The cell system of the present invention includes at least one type of cell bound to at least one chimeric peptide of the present invention. Suitable types of cells include any cell capable of binding to at least one peptide of the present invention. Examples of such cells may include, but are not limited to, fibroblasts, endothelial cells, chondrocytes, neuroblastoma cells, melanoma cells, kidney cells, liver cells, pancreatic cells, thyroid cells, glial cells, smooth muscle cells, mouse mammary carcinoma cells, bone or cartilage forming cells, and combinations thereof.

The cellular structure of the present invention may be further used for enhanced culturing specific/selected cells. At least one type of cell may be allowed to bind to the chimeric peptides of the present invention. The selected cells are then grown in culture medium under suitable cell culture conditions. The advantage of such cellular structures is that the M-tides and the chimeric peptides of the present invention enable the formation of a 3-D structures, for example, 3-D structure around Sepharose beads, glass or collagen in any desired geometry, of specific cells thereby rendering the structure attractive for selecting specific cell types. Hereinafter, the term "structure" includes but is not limited to the term "matrix".

The aforementioned cellular structure of the invention may be used for improved implantation of cells or medical devices in a subject in need thereof. The selected cells attached to the structure may be maintained and allowed to proliferate and when ready for implantation or for moving to another cell growth system, the cell-coated structure may be removed from the culture medium. Advantageously, using the cellular structure of the present invention, the cells are removed as a whole tissue culture, avoiding a traumatic cellular detachment that is commonly used for cell removal. Conventional methods for removing cells from culture medium often require trypsinization, which may damage the cells for example by damaging certain receptors on the cells. The ability to transfer cells from one environment to another by moving the cellular culture as a whole, on a 3-D structure or matrix, also enables the cells to be re-seeded into fresh culture medium with minimal damage to the cells.

The cell structures of the present invention may be further used for culturing cells at a higher density than density of conventional cell cultures. High density cell cultures are particularly useful for the production of recombinant proteins and for other types of cell culture products. The cell culture system of the present invention may be thus used for transfecting cells with various vectors, viruses, nucleic acids and the like, in order to facilitate the production of the cell culture products or to genetically modify the cells themselves.

The chimeric peptides of the present invention may be further used for separating cells with high affinity to said peptides from cells which are not capable of binding said peptide(s). For example, a peptide of the present invention in a structure, such as a matrix or a Sepharose bead, as described hereinabove, may be incubated with a mixture of cells in solution, under suitable conditions to enable binding only those cells which are capable of binding the peptide. The resulting cellular structure or matrix may be isolated for further processing.

Additionally, a chimeric peptide of the present invention may be attached to a substantially immobile support (such as the surface of a prosthetic device), and exposed to tissue culture comprising desired cells. The desired cells may coat the surface of the prosthetic device, thereby rendering it suitable for implantation.

Additionally, the chimeric peptide of the present invention attached to a solid surface may be applied for diagnostic purposes. For example, the presence or absence of a certain type of cell, or of a certain cell function, could be determined by examining whether the cell is bound to the peptide using suitable detection assays, such as fluorescent cell sorting. Examples of cell functions which can be diagnosed include, but are not limited to, the ability to respond to a chemotactic or an attachment signal.

These functions would be assessed by the determination of cell binding to the peptide-coated structure. The determination of cell binding could be performed by the ability to separate the cell from a solution or mixture of different cell types, as described previously.

Alternatively, the peptide of the invention may be labeled with a reporter, such as a fluorescent or a radioactive moiety. The reporter would be used to determine if the peptide had bound to any of the cells, thus enabling the presence or absence of the cell type, or of a certain cell function, to be determined.

Examples of suitable fluorescent moieties include, but are not limited to, fluorescein, FITC (fluorescein iso-thio-cyanate), rhodamine and Texas red. Examples of suitable radioactive moieties include, but are not limited to, phosphorous 32, iodine 131 and tritium. The reporter could be attached to the peptide during synthesis or alternatively post-synthesis, according to well known methods in the art.

The chimeric peptides of the present invention are also contemplated as being useful for the formation of a therapeutic structure of cells. Examples of the therapeutic structures include, but are not limited to, a gel, a prosthetic device and a collagen sheet. At least one peptide of the present invention would be attached to the therapeutic structure, for example by a covalent bond formed with a chemical cross-linking reagent as is well known in the art, or with fibrin glue. The cells would then be allowed to attach to the peptide on the therapeutic structure, for example through cell culture or by the separation methods described above. The choice of cells will depend upon the type of tissue being contacted and the desired therapeutic structure, and could potentially include any cell type which is capable of binding to at least one peptide of the present invention.

Example 6

Methods for Treatment Using the Peptides of the Invention

The chimeric peptides of the present invention are contemplated as being useful for treatment of a subject with a disease condition in which the condition can be ameliorated or cured, at least in part, through cell chemotaxis or proliferation, or by transplantation of cells. Examples of such a condition include, but are not limited to, the presence of a wound and diseases characterized by an absence of a cell product. The term "wound" includes any disruption of the normal integrity of an organ of the subject. Examples of such an organ include, but are not limited to, the skin, the abdominal cavity, the intestine, the heart, the lungs, any blood vessel, any bone, the pancreas, the liver, a kidney, the reproductive organs or the stomach.

The wound may be present as the result of a surgical intervention or as the result of a non-surgical intervention. The surgical intervention could be either planned or as the result of a medical emergency. The non-surgical intervention could be a burn, an ulcer, a laceration or any type of accidental injury or trauma.

Methods of treatment with the haptotactic peptides of the present invention for surgical intervention could include placing one or more of the peptides at the site of the surgical intervention, in order to increase the efficiency of the wound healing process. The one or more peptides could be placed at the site of the surgical intervention before surgery, particularly for emergency surgery, during surgery or after surgery. The one or more peptides could be included in a therapeutic composition, as described in Example 6 below.

Methods of treatment of non-surgical interventions would include placing one or more of the peptides at the site of the non-surgical intervention, in order to increase the efficiency of the wound healing process. The one or more peptides could also be included in a therapeutic composition, as described in Example 6 below.

The one or more peptides of the present invention could be placed at the site of the surgical or non-surgical intervention once, or repeatedly, depending upon the type and gravity of the wound which was sustained. The concentration and rate of treatment, if repeated, could easily be determined by one of ordinary skill in the art.

Examples of diseases characterized by an absence of a cell product include, but are not limited to, diabetes mellitus, hemophilia A (factor VIII deficiency), hemophilia B (factor IX) deficiency and Parkinson's disease. These diseases could be ameliorated or cured by introducing, to a subject in need thereof, cells which produce the necessary cell metabolite or product. These cells may be initially transformed by a vector comprising the nucleic acid sequence coding for the desired metabolite or product (e.g. insulin), as is well known in the art. Alternatively cells may be initially transformed by a vector comprising the nucleic acid sequence coding for a peptide or a protein that is capable of driving the cells to produce the desired cell product, for example through an enzymatic reaction or reactions. In any case, the cell would then be able to produce the desired cell product after such preparation.

Once prepared, the cells would be attached to a chimeric peptide of the present invention, which would in turn be incorporated within a suitable cell structure as described hereinabove. The cell structure may be administered to the subject in need thereof and then produce the necessary cell metabolite or product. The advantage of using the cell structure according to the present invention is that the cells would remain substantially localized, being attached to the surface of a matrix or the like, however the cell products is allowed entering the bloodstream if desired. Thus, by using the chimeric peptide of the present invention, the cell structure may be used for treating a disease requiring cell metabolites or products for healing.

Example 7

Formulations of Chimeric Peptides

The chimeric peptides of the present invention may be administered to a subject in need thereof, via different routes of administration, which are well known in the art. For example, administration may be done topically (including opthalmically, vaginally, rectally, intranasally), orally, or parenterally, for example by intravenous drip or intraperitoneal, subcutaneous, or intramuscular injection. Hereinafter, the term "subject" refers to the human or lower animal.

Formulations for topical administration include but are not limited to lotions, ointments, gels, creams, suppositories, drops, attached to liposomal formulations, attached to viral vectors, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives, liposomal formulations, viral vectors, and said peptides in suspension of nanoparticles.

For treating a wound, the chimeric peptides of the present invention, preferably, pharmaceutical compositions comprising same, are laid onto the wound bed. The pharmaceutical composition may further include suitable pharmaceutically acceptable carrier(s). For example, the pharmaceutical composition may further include lasered or heated albumin to accelerate wound healing, minimize scarring, accelerate the rate of deposition of new extracellular matrix and augment angiogenesis.

As another example, a polymer may be made of subunits of at least one of the peptides of the present invention, such that a plurality of these peptides would be linked to form the peptide polymer. The peptides may be linked with a chemical cross-linking moiety. More than one of the peptides of the present invention may be used to form the polymer. Alternatively, at least one of the peptides of the present invention could be attached to a biologically acceptable synthetic polymer, again through a suitable cross-linking moiety, to form a co-polymer. In either case, the resultant peptide polymer or co-polymer may be used to fabricate microparticles which could either be included in a composition according to the present invention, or else could be used form cell structures as described in Example 6 above.

The composition for wound treatment can also include at least one bioactive agent. Suitable bioactive agents include, but are not limited to, drugs, neurologics, vitamins, vitamin derivatives, growth factors, glucocorticosteroids, steroids, antibiotics, antibacterial compounds including bacteriocidal and bacteriostatic compounds, antiparasitic compounds, tumoricidal compounds, tumoristatic compounds, toxins, enzymes, enzyme inhibitors, proteins, peptides, minerals, neurotransmitters, lipoproteins, glycoproteins, immunomodulators, immunoglobulins and fragments thereof, fatty acid derivatives, polysaccharides, cell receptor binding molecules, anti-inflammatories, anti-glaucomic compounds, mydriatic compounds, anesthetics, nucleic acids, polynucleotides and the like.

The therapeutic composition could also include at least one-type of cell in a structured format, as described in Example 6 above. For example, the previously described sheet structure for cell culture could be placed on the wound in order to both protect the wound during the healing process, and to promote the wound healing process itself. The structure could also be the previously described haptotactic peptide-containing gel, which would be placed on the wound for transplanting the cells onto the site of the wound, and would then be able to promote the wound healing process. Other examples of such structured cell systems could also be used as part of the therapeutic composition of the present invention for wound healing. When used for wound healing, suitable cell types include, but are not limited to, fibroblasts, smooth muscle cells, endothelial cells, chondrocytes, bone or cartilage forming cells, and combinations thereof.

Combinations of any two or more of these different components of therapeutic compositions are also possible as therapeutic Compositions of the present invention.

Dosing is dependent on the severity of the symptoms and on the responsiveness of the subject to the peptide or fragments of the present invention. Persons of ordinary skill in the art can easily determine optimum dosages, dosing methodologies and repetition rates.

Example 8

Analytic Means

The peptides of the present invention are also contemplated as tools for performing analysis of other systems, and for further research and development. For example, the chimeric peptides could be used to identify and isolate cell receptors. As described previously, the peptide could be labeled with a reporter, such as a fluorescent or radioactive moiety. The reporter would be used to determine if the peptide had bound to any of the cells, thus enabling the presence or absence of the cell type, or of a certain cell function, to be determined.

Examples of suitable fluorescent moieties include, but are not limited to, FITC (fluorescein), rhodamine and Texas red. Examples of suitable radioactive moieties include, but are not limited to, phosphorous-32, iodine-131 and tritium. The reporter could be attached to the peptide during synthesis or alternatively post-synthesis, according to well known methods in the art. Thus, the ability of the peptide to bind to a novel receptor or other protein could be determined according to a binding assay.

In addition, the peptides of the present invention could be used to design analogues, such as non-peptide mimetics, of these peptides. Such non-peptide mimetics could be used for therapeutic purposes, for example. Non-peptide compounds are potentially easier to administer, since peptides are preferably administered nasally or parenterally, for example, while non-peptide compounds could potentially be administered orally. Furthermore, particular properties of each peptide could be selected or augmented by designing a specific analogue. Thus, the peptides of the present invention could potentially yield many new and different types of therapeutic medicaments.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A chimeric peptide capable of inducing cell attachment to a surface to which it is covalently bound, comprising: SEQ ID NO:32.

2. The chimeric peptide of claim 1, wherein the chimeric peptide induces cell attachment to a surface to which it is covalently bound and wherein the number of cells attached to the surface is at least 50% greater than the number of cells attached to the surface in the absence of the peptide.

3. A composition comprising the chimeric peptide of claim 1 and a pharmaceutically acceptable carrier.

4. The composition of claim 3, wherein the chimeric peptide is bound to a tag selected from a fluorescent tag and a radioactive tag.

5. The composition of claim 3, further comprising at least one biological agent.

6. The composition of claim 5, wherein the at least one biological agent is selected from the group consisting of vitamins, vitamin derivatives, growth factors, glucocorticosteroids, steroids, antibiotics, toxins, enzymes, enzyme inhibitors, immunomodulators, immunoglobulins and fragments thereof, fatty acid derivatives, polysaccharides, cell receptor binding molecules, anti-inflammatories, nucleic acids, polynucleotides and a therapeutic agent.

7. The composition of claim 3, wherein the chimeric peptide is covalently attached to a solid surface.

8. The composition of claim 7, wherein the chimeric peptide is covalently attached to the solid surface of a medical implant.

9. The composition of claim 8, further comprising a plurality of cells selected from the group consisting of mesenchymal cells, parenchymal cells, fibroblasts, endothelial cells, chondrocytes, kidney cells, liver cells, pancreatic cells, thyroid cells, glial cells, astrocytes, smooth muscle cells and myofibroblasts, wherein the chimeric peptide is further attached to at least one cell of the plurality of cells.

10. A polymer composition, comprising a plurality of subunits, each of the subunits comprising at least one chimeric peptide comprising: SEQ ID NO:32.

11. The chimeric peptide of claim 1, having the amino acid sequence set forth in SEQ ID NO: 32.

12. The chimeric peptide of claim 1, consisting of the amino acid sequence of SEQ ID NO: 32.

* * * * *

SEQUENCE LISTING

<160> NUMBER OF SEQ ID NOS: 49

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Val Phe Gln Lys Arg Leu Asp Gly Ser Val Asp Phe Lys Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 2

Val Ile Gln Asn Arg Gln Asp Gly Ser Val Asp Phe Gly Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 3

Val Phe Leu Arg Arg Lys Asn Gly Arg Glu Asn Phe Tyr Gln
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Val Phe Gln Arg Arg Met Asp Gly Gln Thr Asp Phe Trp Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 5

Val Phe Gln Arg Arg Gln Asn Gly Gln Thr Asp Phe Phe Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: SYNTHETIC PEPTIDE

```
<400> SEQUENCE: 6

Val Ile Gln His Arg Glu Asp Gly Ser Leu Asp Phe Gln Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 7

Ile Ile Gln Arg Arg Glu Asp Gly Ser Val Asp Phe Gln Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 8

Val Phe Gln Lys Arg Phe Asn Gly Ser Val Ser Phe Phe Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 9

Leu Gly Gly Ala Lys Gln Ala Gly Asp Val
1               5                   10

<210> SEQ ID NO 10
<211> LENGTH: 27
<212> TYPE: PRT
<213> ORGANISM: Artificial Sequence
<220> FEATURE:
<223> OTHER INFORMATION: Synthetic peptide

<400> SEQUENCE: 10

Val Tyr Cys Glu Ile Asp Gly Ser Gly Asn Gly Trp Thr Val Phe Gln
1               5                   10                  15

Lys Arg Leu Asp Gly Ser Val Asp Phe Lys Lys
            20                  25

<210> SEQ ID NO 11
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 11

Val Tyr Cys Asp Met Asn Thr Glu Asn Gly Gly Trp Thr Val Ile Gln
1               5                   10                  15

Asn Arg Gln Asp Gly Ser Val Asp Phe Gly Arg
            20                  25
```

```
<210> SEQ ID NO 12
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 12

Val Phe Cys Asp Met Thr Ser Asp Gly Gly Gly Trp Ile Val Phe Leu
1               5                   10                  15

Arg Arg Lys Asn Gly Arg Glu Asn Phe Tyr Gln
            20                  25

<210> SEQ ID NO 13
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 13

Val Phe Cys Asp Met Glu Thr Asp Gly Gly Gly Trp Leu Val Phe Gln
1               5                   10                  15

Arg Arg Met Asp Gly Gln Thr Asp Phe Trp Arg
            20                  25

<210> SEQ ID NO 14
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 14

Val Tyr Cys Asp Met Thr Thr Asp Gly Gly Gly Trp Ile Val Phe Gln
1               5                   10                  15

Arg Arg Gln Asn Gly Gln Thr Asp Phe Phe Arg
            20                  25

<210> SEQ ID NO 15
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 15

Val Phe Cys Asn Met Asp Val Asn Gly Gly Gly Trp Thr Val Ile Gln
1               5                   10                  15

His Arg Glu Asp Gly Ser Leu Asp Phe Gln Arg
            20                  25

<210> SEQ ID NO 16
<211> LENGTH: 26
<212> TYPE: PRT
<213> ORGANISM: Artificial Sequence
<220> FEATURE:
<223> OTHER INFORMATION: SYNTHETIC PEPTIDE

<400> SEQUENCE: 16

Phe Tyr Cys Asp Met Glu Ala Gly Gly Gly Trp Thr Ile Ile Gln Arg
1               5                   10                  15

Arg Glu Asp Gly Ser Val Asp Phe Gln Arg
            20                  25
```

```
<210> SEQ ID NO 17
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 17

Val Phe Cys Asp Met Thr Thr Glu Gly Gly Lys Trp Thr Val Phe Gln
1               5                   10                  15

Lys Arg Phe Asn Gly Ser Val Ser Phe Phe Arg
            20                  25

<210> SEQ ID NO 18
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 18

Lys Thr Arg Trp Tyr Ser Met Lys Lys Thr Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Lys Gly Pro Ser Tyr Ser Leu Arg Ser Thr Thr
1               5                   10

<210> SEQ ID NO 20
<211> LENGTH: 19
<212> TYPE: PRT
<213> ORGANISM: Artificial Sequence
<220> FEATURE:
<223> OTHER INFORMATION: SYNTHETIC PEPTIDE

<400> SEQUENCE: 20

Lys Gly Ser Gly Tyr Ser Leu Lys Ala Thr Thr Met Met Ile Arg Pro
1               5                   10                  15

Ala Asp Phe

<210> SEQ ID NO 21
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 21

Lys Gly Phe Glu Phe Ser Val Pro Phe Thr Glu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide
```

```
<400> SEQUENCE: 22

Lys Gly Phe Tyr Tyr Ser Leu Lys Arg Thr Glu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 23

Lys Gly Ser Trp Tyr Ser Met Arg Lys Met Ser
1               5                   10

<210> SEQ ID NO 24
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 24

Arg Gly Ala Asp Tyr Ser Leu Arg Ala Val Arg Met Lys Ile Arg Pro
1               5                   10                  15

Leu Val Thr Gln
            20

<210> SEQ ID NO 25
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 25

Lys Gly His Glu His Ser Ile Gln Phe Ala Glu Met Lys Leu Arg Pro
1               5                   10                  15

Ser Asn Phe Arg
            20

<210> SEQ ID NO 26
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 26

Lys Thr Arg Trp Tyr Ser Met Lys Lys Thr Thr Met Lys Ile Ile Pro
1               5                   10                  15

Phe Asn Arg Leu
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic peptide

<400> SEQUENCE: 27

Lys Gly Pro Ser Tyr Ser Leu Arg Ser Thr Thr Met Met Ile Arg Pro
1               5                   10                  15

Leu Asp Phe
```

-continued

```
<210> SEQ ID NO 28
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 28

Lys Gly Phe Glu Phe Ser Val Pro Phe Thr Glu Met Lys Leu Arg Pro
1               5                   10                  15

Arg Asn Phe Arg
            20

<210> SEQ ID NO 29
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 29

Lys Gly Phe Tyr Tyr Ser Leu Lys Arg Thr Glu Met Lys Ile Arg Arg
1               5                   10                  15

Ala

<210> SEQ ID NO 30
<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 30

Lys Gly Ser Trp Tyr Ser Met Arg Lys Met Ser Met Lys Ile Arg Pro
1               5                   10                  15

Phe Phe Pro Gln Gln
            20

<210> SEQ ID NO 31
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 31

Lys Thr Arg Trp Tyr Ser Met Lys Lys Thr Thr Met Lys
1               5                   10

<210> SEQ ID NO 32
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 32

Lys Thr Arg Trp Tyr Ser Met Lys Lys Thr Thr Met Lys Val Phe Gln
1               5                   10                  15

Lys Arg Leu Asp Gly Ser Val Asp Phe Lys Lys
            20                  25

<210> SEQ ID NO 33
<211> LENGTH: 27
<212> TYPE: PRT
<213> ORGANISM: Artificial Sequence
```

```
<220> FEATURE:
<223> OTHER INFORMATION: SYNTHETIC PEPTIDE

<400> SEQUENCE: 33

Lys Gly Ser Trp Tyr Ser Met Arg Lys Met Ser Met Lys Val Ile Gln
1               5                   10                  15

Asn Arg Gln Asp Gly Ser Val Asp Phe Gly Arg
            20                  25

<210> SEQ ID NO 34
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 34

Lys Gly Phe Glu Phe Ser Val Pro Phe Thr Glu Met Lys Val Phe Gln
1               5                   10                  15

Arg Arg Met Asp Gly Gln Thr Asp Phe Trp Arg
            20                  25

<210> SEQ ID NO 35
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 35

Lys Gly Pro Ser Tyr Ser Leu Arg Ser Thr Thr Met Met Val Ile Gln
1               5                   10                  15

His Arg Glu Asp Gly Ser Leu Asp Phe Gln Arg
            20                  25

<210> SEQ ID NO 36
<211> LENGTH: 27
<212> TYPE: PRT
<213> ORGANISM: Artificial Sequence
<220> FEATURE:
<223> OTHER INFORMATION: SYNTHETIC PEPTIDE

<400> SEQUENCE: 36

Lys Gly Phe Tyr Tyr Ser Leu Lys Arg Thr Glu Met Lys Val Phe Gln
1               5                   10                  15

Lys Arg Phe Asn Gly Ser Val Ser Phe Phe Arg
            20                  25

<210> SEQ ID NO 37
<211> LENGTH: 14
<212> TYPE: PRT
<213> ORGANISM: Artificial Sequence
<220> FEATURE:
<223> OTHER INFORMATION: Synthetic peptide

<400> SEQUENCE: 37

Leu Ile Gln Gln Arg Met Asp Gly Ser Leu Asn Phe Asn Arg
1               5                   10

<210> SEQ ID NO 38
<211> LENGTH: 27
<212> TYPE: PRT
<213> ORGANISM: Artificial Sequence
<220> FEATURE:
<223> OTHER INFORMATION: SYNTHETIC PEPTIDE
```

-continued

```
<400> SEQUENCE: 38

Arg Gly Ala Asp Tyr Ser Leu Arg Ala Val Arg Met Lys Leu Ile Gln
1               5                   10                  15

Gln Arg Met Asp Gly Ser Leu Asn Phe Asn Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: X is any amino acid

<400> SEQUENCE: 39

Lys Thr Arg Trp Tyr Ser Met Lys Lys Thr Thr Met Lys Xaa Val Phe
1               5                   10                  15

Gln Lys Arg Leu Asp Gly Ser Val Asp Phe Lys Lys
            20                  25

<210> SEQ ID NO 40
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (14)..(14)
<223> OTHER INFORMATION: X is any amino acid

<400> SEQUENCE: 40

Lys Gly Ser Trp Tyr Ser Met Arg Lys Met Ser Met Lys Xaa Val Ile
1               5                   10                  15

Gln Asn Arg Gln Asp Gly Ser Val Asp Phe Gly Arg
            20                  25

<210> SEQ ID NO 41
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (14)..(14)
<223> OTHER INFORMATION: X is any amino acid

<400> SEQUENCE: 41

Lys Gly Phe Glu Phe Ser Val Pro Phe Thr Glu Met Lys Xaa Val Phe
1               5                   10                  15

Gln Arg Arg Met Asp Gly Gln Thr Asp Phe Trp Arg
            20                  25

<210> SEQ ID NO 42
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (14)..(14)
<223> OTHER INFORMATION: X is any amino acid
```

-continued

```
<400> SEQUENCE: 42

Lys Gly Pro Ser Tyr Ser Leu Arg Ser Thr Thr Met Met Xaa Val Ile
1               5                   10                  15

Gln His Arg Glu Asp Gly Ser Leu Asp Phe Gln Arg
            20                  25

<210> SEQ ID NO 43
<211> LENGTH: 28
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MISC_FEATURE
<222> LOCATION: (14)..(14)
<223> OTHER INFORMATION: X is any amino acid

<400> SEQUENCE: 43

Lys Gly Phe Tyr Tyr Ser Leu Lys Arg Thr Glu Met Lys Xaa Val Phe
1               5                   10                  15

Gln Lys Arg Phe Asn Gly Ser Val Ser Phe Phe Arg
            20                  25

<210> SEQ ID NO 44
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (14)..(14)
<223> OTHER INFORMATION: X is any amino acid

<400> SEQUENCE: 44

Arg Gly Ala Asp Tyr Ser Leu Arg Ala Val Arg Met Lys Xaa Leu Ile
1               5                   10                  15

Gln Gln Arg Met Asp Gly Ser Leu Asn Phe Asn Arg
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic peptide

<400> SEQUENCE: 45

Val Tyr Cys Glu Ile Asp Gly Ser Gly Asn Gly Trp Thr Val Phe Gln
1               5                   10                  15

Lys Arg Leu Asp Gly Ser Leu Asp Phe Lys Lys
            20                  25

<210> SEQ ID NO 46
<211> LENGTH: 27
<212> TYPE: PRT
<213> ORGANISM: Gallus gallus

<400> SEQUENCE: 46

Val Tyr Cys Glu Ile Asp Thr Tyr Gly Asn Gly Trp Thr Val Leu Gln
1               5                   10                  15

Arg Arg Leu Asp Gly Ser Glu Asp Phe Arg Arg
            20                  25
```

```
<210> SEQ ID NO 47
<211> LENGTH: 27
<212> TYPE: PRT
<213> ORGANISM: Artificial Sequence
<220> FEATURE:
<223> OTHER INFORMATION: Synthetic peptide

<400> SEQUENCE: 47

Val Tyr Cys Glu Thr Asp Gly Pro Gly Asn Gly Trp Thr Glu Phe Lys
1               5                   10                  15

Lys Arg Leu Asp Gly Ser Val Asp Phe Leu Lys
            20                  25

<210> SEQ ID NO 48
<211> LENGTH: 26
<212> TYPE: PRT
<213> ORGANISM: Petromyzon marinus

<400> SEQUENCE: 48

Val Phe Cys Glu Ile Glu Asn Gly Asn Gly Trp Thr Val Ile Gln His
1               5                   10                  15

Arg His Asp Gly Ser Val Asn Phe Thr Arg
            20                  25

<210> SEQ ID NO 49
<211> LENGTH: 20
<212> TYPE: PRT
<213> ORGANISM: Homo sapiens

<400> SEQUENCE: 49

Ser Glu Ala Asp His Glu Gly Thr His Ser Thr Lys Arg Gly His Ala
1               5                   10                  15

Lys Ser Arg Pro
            20
```